US006793890B2

(12) United States Patent
Morales et al.

(10) Patent No.: US 6,793,890 B2
(45) Date of Patent: Sep. 21, 2004

(54) RAPID TISSUE PROCESSOR

(75) Inventors: Azorides R. Morales, Miami, FL (US); Ervin Essenfeld, Caracas (VE); Harold Essenfeld, Caracas (VE); Harold D. Kimrey, Knoxville, TN (US)

(73) Assignee: The University of Miami, Miami, FL (US)

( * ) Notice: Subject to any disclaimer, the term of this patent is extended or adjusted under 35 U.S.C. 154(b) by 258 days.

(21) Appl. No.: 09/735,918

(22) Filed: Dec. 14, 2000

(65) Prior Publication Data

US 2001/0051365 A1 Dec. 13, 2001

Related U.S. Application Data

(63) Continuation-in-part of application No. 09/136,292, filed on Aug. 19, 1998, now Pat. No. 6,207,408.
(60) Provisional application No. 60/170,545, filed on Dec. 14, 1999, and provisional application No. 60/056,102, filed on Aug. 20, 1997.

(51) Int. Cl.[7] .................................................. B01L 3/00
(52) U.S. Cl. ............................ 422/99; 422/62; 422/63; 422/104; 435/40.5; 435/40.51; 435/40.52; 436/46; 436/63; 436/64; 436/174; 436/176
(58) Field of Search ............................ 422/62, 63, 65, 422/73, 99, 104; 436/43, 44, 46, 47, 63, 64, 174, 176; 435/40.5, 40.51, 40.52

(56) References Cited

U.S. PATENT DOCUMENTS

| 2,150,757 A | 3/1939 | Bodine |
| 2,684,925 A | 7/1954 | Ferrari, Jr. |
| 3,389,052 A | 6/1968 | Ehrenreich et al. |
| 3,546,334 A | 12/1970 | Lerner et al. |

(List continued on next page.)

FOREIGN PATENT DOCUMENTS

| EP | 0562877 | 9/1993 |
| EP | 0 680 243 A2 | 4/1995 |
| EP | 0 822 403 A1 | 8/1996 |
| EP | 0822403 | 2/1998 |
| WO | WO 86/06479 | 11/1986 |
| WO | WO 98/05938 | 2/1998 |
| WO | WO 99/09390 | 2/1999 |

OTHER PUBLICATIONS

J. Ben–Ezra et al., "Effect of Fixation on the Amplification of Nucleic Acids from Paraffin–embedded Material by the Polymerase Chain Reaction", *The Journal of Histochemistry and Cytochemistry*, vol. 39, No. 3, pp. 351–354, 1991.

M.E. Boon et al., "The Two–Step Vacuum–Microwave Method for Histoprocessing", *Microwave Newsletter*, vol. 33 No. 4, pp. 349–358, Nov. 1995.

D.G. Bostwick, et al., "Establishment of the Formalin–Free Surgical Pathology Laboratory", *Arch. Pathol. Lab Med.*, vol. 118, pp. 298–302, Mar. 1994.

(List continued on next page.)

*Primary Examiner*—Jill Warden
*Assistant Examiner*—Dwayne K Handy
(74) *Attorney, Agent, or Firm*—Nixon & Vanderhye PC

(57) ABSTRACT

An improved microwave unit and tissue processor system incorporating the unit are provided for use in rapid tissue processing. The microwave unit may be comprised of an energy source, a waveguide transmitting the microwave energy to a reaction chamber, and the reaction chamber being adapted to process tissue specimens for histology. The unit provides gentle and uniform heating, with minimal heat loss and escape of volatile chemicals. The system may be operated continuously and/or batchwise, by manual operation or automatically. The automated system may be operated with continuous throughput to obtain the advantages of the invention such as, for example, rapid processing under two hours and/or preservation of cell structure and tissue architecture.

33 Claims, 14 Drawing Sheets

U.S. PATENT DOCUMENTS

| | | |
|---|---|---|
| 3,674,040 A | 7/1972 | Howells et al. |
| 3,892,197 A | 7/1975 | Kinney et al. |
| 3,961,097 A | 6/1976 | Gravlee, Jr. |
| 3,995,022 A | 11/1976 | Heanley et al. |
| 4,099,483 A | 7/1978 | Henderson |
| 4,141,312 A | 2/1979 | Louder et al. |
| 4,199,558 A | 4/1980 | Henderson |
| 4,221,823 A | 9/1980 | Pearson et al. |
| 4,300,243 A | 11/1981 | Baumgartner |
| 4,545,831 A | 10/1985 | Ornstein |
| 4,656,047 A | 4/1987 | Kok et al. |
| 4,670,386 A | 6/1987 | Sugaar |
| 4,681,996 A | 7/1987 | Collins et al. |
| 4,784,873 A | 11/1988 | Kienecker et al. |
| 4,835,354 A | 5/1989 | Collins et al. |
| 4,839,194 A | 6/1989 | Malluche et al. |
| 4,882,128 A | 11/1989 | Hukvari et al. |
| 4,891,239 A | 1/1990 | Dudley et al. |
| 4,911,915 A | 3/1990 | Fredenburgh |
| 4,992,763 A | 2/1991 | Bert et al. |
| 4,994,237 A * | 2/1991 | Login et al. .................. 422/21 |
| 5,023,187 A | 6/1991 | Koebler et al. |
| 5,030,929 A | 7/1991 | Moeller |
| 5,049,510 A | 9/1991 | Repasi et al. |
| 5,068,086 A | 11/1991 | Sklenak et al. |
| 5,089,288 A | 2/1992 | Berger |
| 5,104,640 A | 4/1992 | Stokes |
| 5,122,633 A | 6/1992 | Moshammer et al. |
| 5,230,865 A | 7/1993 | Hargett et al. |
| 5,244,787 A | 9/1993 | Key et al. |
| 5,256,571 A | 10/1993 | Hurley et al. |
| 5,289,140 A | 2/1994 | Jorgenson et al. |
| 5,318,795 A | 6/1994 | Stokes et al. |
| 5,387,397 A | 2/1995 | Strauss et al. |
| 5,401,625 A | 3/1995 | Robinson |
| 5,431,952 A | 7/1995 | Ocello |
| 5,432,056 A | 7/1995 | Hartman et al. |
| 5,460,797 A | 10/1995 | Ryan |
| 5,532,462 A | 7/1996 | Butwell et al. |
| 5,625,706 A | 4/1997 | Lee et al. |
| 5,672,696 A | 9/1997 | Wang et al. |
| 5,679,333 A | 10/1997 | Dunphy |
| 5,712,605 A | 1/1998 | Flory et al. |
| 5,758,033 A * | 5/1998 | Berstein et al. ................ 395/80 |
| 5,782,897 A | 7/1998 | Carr |
| 5,796,080 A | 8/1998 | Jennings et al. |
| 5,830,417 A | 11/1998 | Kingston |
| 5,849,517 A | 12/1998 | Ryan |
| 5,875,286 A | 2/1999 | Bernstein et al. |
| 6,011,247 A * | 1/2000 | Grillo et al. ................ 219/686 |
| 6,042,874 A | 3/2000 | Visinoni et al. |
| 6,072,086 A | 6/2000 | James et al. |
| 6,183,995 B1 | 2/2001 | Burmer et al. |
| 6,204,375 B1 | 3/2001 | Lader |
| 6,207,408 B1 | 3/2001 | Essenfeld et al. |
| 6,248,535 B1 | 6/2001 | Danenberg et al. |
| 6,258,329 B1 * | 7/2001 | Mutterer, Jr. et al. ... 422/186.29 |
| 6,268,596 B1 * | 7/2001 | Lauf et al. .................. 219/687 |
| 6,291,180 B1 | 9/2001 | Chu |

OTHER PUBLICATIONS

I. Dimulescu et al., "Characterization of RNA in Cytologic Samples Preserved in a Methano–Based Collection Solution", *Molecular Diagnosis*, vol. 3, No. 2, pp. 67–72, Jun. 1998.

R.D. Foss, et al., "Effects of FIxative and Fixation Time on the Extraction and Polymerase Chain Reaction Amplification of RNA from Paraffin–Embedded Tissue", *Diagn. Mol. Pathol.*, vol. 3, No. 3, pp. 148–155, 1994.

W.J. Frable, "Cytology Automation", *Am. J. Clin. Pathology*, pp. 121–122, Feb. 1994.

S.M. Goldsworthy, "Effects of Fixation of RNA Extraction and Amplification from Laser Capture Microdissected Tissue", *Molecular Carcinogenesis*, vol. 25, pp. 86–91, 1999.

M.L. Hutchintson, "Homogeneous Sampling Accounts for the Increased Diagnostic Accuracy Using the ThinPrep™ Processor", Am. J. Clin. *Pathology*, vol. 101, No. 2, pp. 215–219, Feb. 1994.

L.P. Kok et al., "Ultrarapid Vacuum–Microwave Histoprocessing", *Histochemical Journal*, vol. 27, pp. 411–419, 1995.

M. Koopmans et al., "Optimization of Extraction and PCR Amplification of RNA Extracts from Paraffin–Embedded Tissue in Different FIxatives", *Journal of Virological Methods*, vol. 43, pp. 189–204, 1993.

P. Maxwell et al., "Use of Alcohol Fixed Cytospins Protected by 10% Polyethylene Glycol in Immunocytology External Quality Assurance", *Journal Clin. Pathol.*, vol. 52, pp. 141–144, 1999.

W. Möller et al., "Chemical Dehydration for Rapid Paraffin Embedding", *Biotechnic & Histochemistry*, vol. 69, No. 5, pp. 289–290, 1994.

Y. Sato et al., "A Simplified Technique of Tissue Processing and Paraffin Embedding With Improved Preservation of Antigens of Immunostaining", *Am. J. Pathol.*, vol. 125, pp. 431–435, Dec. 1986.

Y. Sato et al., "The Amex Method: A Multipurpose Tissue–Processing . . . Slot–Blot Hybridization Analysis", *Journal of Pathology*, vol. 163, pp. 81–85 1991.

R. Takahashi et al., "Freeze Substitution And Freeze . . . for Immunostaining", *Acta Cytologica*, vol. 40, No. 3, pp. 396–400, May–Jun. 1996.

"Biogenex Victorious in Infringement Suit", *Biotechnology Law Report*, vol. 478, No. 4, Jul.–Aug. 1997.

Sakura Tissue–Tek VIP Vacuum Infiltration Processor Series; Pamphlet (1996).

Multiwax Microcyrstalline Waxes From Sonneborn: The Standard Of The Industry; WITCO Pamphlet.

Sonneborn White Oils: The Clear Choice Since 1903; WITCO Pamphlet (1987).

Paraffin Tissue Processor—HMP 300; Microm; Carl Zeiss Pamphlet.

Shandon/Lipshaw Pathcentre Enclosed Tissue Processor Product Brochure (1995).

Shandon Hypercenter XP Pamphlet (1994).

Tissue–TEk V.I.P. Vacuum Infiltration Processor E150/E300 Series, Operating Manual (1992).

Tissue–Tek V.I.P. Vacuum Infiltration Processor (Bench and Floor Models), Operating Manual (1992).

Ventana Medical Systems Inc., Renaissance Tissue Processor.

Milestone Micromed T/T Mega Microwave Labstation for Pathology.

Zubkova et al., "Acceleration of histologic tissue processing and declacification using a microwave oven", Arkh Patol 59(2):64–66, (Mar.–Apr. 1997) (Abstract only).

Zubkova et al., "Histologic tissue processing in an automated microwave histoprocessor", Arkh Patl 61(3):48–49 May–Jun. 1999 (Abstract only).

Kovacs et al., "Experiences with a new vacuum–accelerated microwave histoprocessor", Orv Hetil 137(27):1479–1483, (Jul. 1996) (Abstract only).

Bellotti et al. "Use of the Microwave Oven for Cell Block Preparation"Acta Cytol 41(2):610–611, (Mar.–Apr. 1997).

Kovacs et al., "Working Experience with a New Vaccum–Accelerated Microwave Histoprocessor", J. Pathol. 180(1): 106–110, (Sep. 1996).

Marani et al., "The Search for Vacuo–Microwave Technique: The Vaccum–Microwave Oven", Eur. J. Morphol. 34(2):123–130, (1996).

Stokes, "Compositions for Fixing Biological Smears on Slides—Comprising non–Aqueous Fixative LIquid, Stabiliser and Solubilising Agent" Biosis Database Accession No. XP002208633 (1992).

Gayle et al. "Evaluation of Clearing and Infiltration Mixtures (CIMs) as Xylene Substitutes for Tissue Processing" Biosis Database Accession No. XP002220503 (1994).

Buesa, "Mineral Oil: The Best Xylene Substitute for Tissue Processing Yet?," The Journal of Histotechnology, vol. 23, No. 2, Jun. 2000, pp. 143–149.

Liotta et al., "Molecular Profiling of Human Cancer," Nature Reviews Genetics, vol. 1, Oct. 2000, pp. 48–55.

Tissue–Tek V.I.P., "Vacuum Infiltration Processor (Bench and Floor Models V.I.P. 1000, 2000 and 3000) Operating Manual," Miles Inc., Second Edition, Sep. 1992, pp. 1.0–9.1.

Tissue–Tek V.I.P., "Vacuum Infiltration Processor E150/E300 Series Operating Manual," Miles Inc., First Edition, Sep. 1993, pp. 1.1–A.8.

www.mopec.com/tpc15.html, "Medite TPC5 Tissue Processor," Mopec Pathology, Laboratory and Morgue Equipment, Dec. 13, 1999, pp. 1–2.

* cited by examiner

FIG. 1

THE PRACTICE OF SURGICAL PATHOLOGY
Conventional Pathway From Surgery to Tissue Diagnosis

DAY 1

Surgery → "grossing" → batching of specimens → batched specimens input into processor → overnight processing

DAY 2

Batched specimens output from processor → block → microtomy → H&E stain → diagnosis

INTERVAL OF TIME FROM SURGERY TO DIAGNOSIS:>22 HOURS

FIG. 2

THE PRACTICE OF SURGICAL PATHOLOGY
Continuous Throughput Method-Pathway From Surgery to Tissue Diagnosis

DAY 1

Surgery →  "grossing" → continuous every 15 min specimens input into 45 min processing system → continuous every 15 min output of specimens from system → block → microtomy → H&E stain → diagnosis

INTERVAL OF TIME FROM SURGERY TO DIAGNOSIS:<2 HOURS

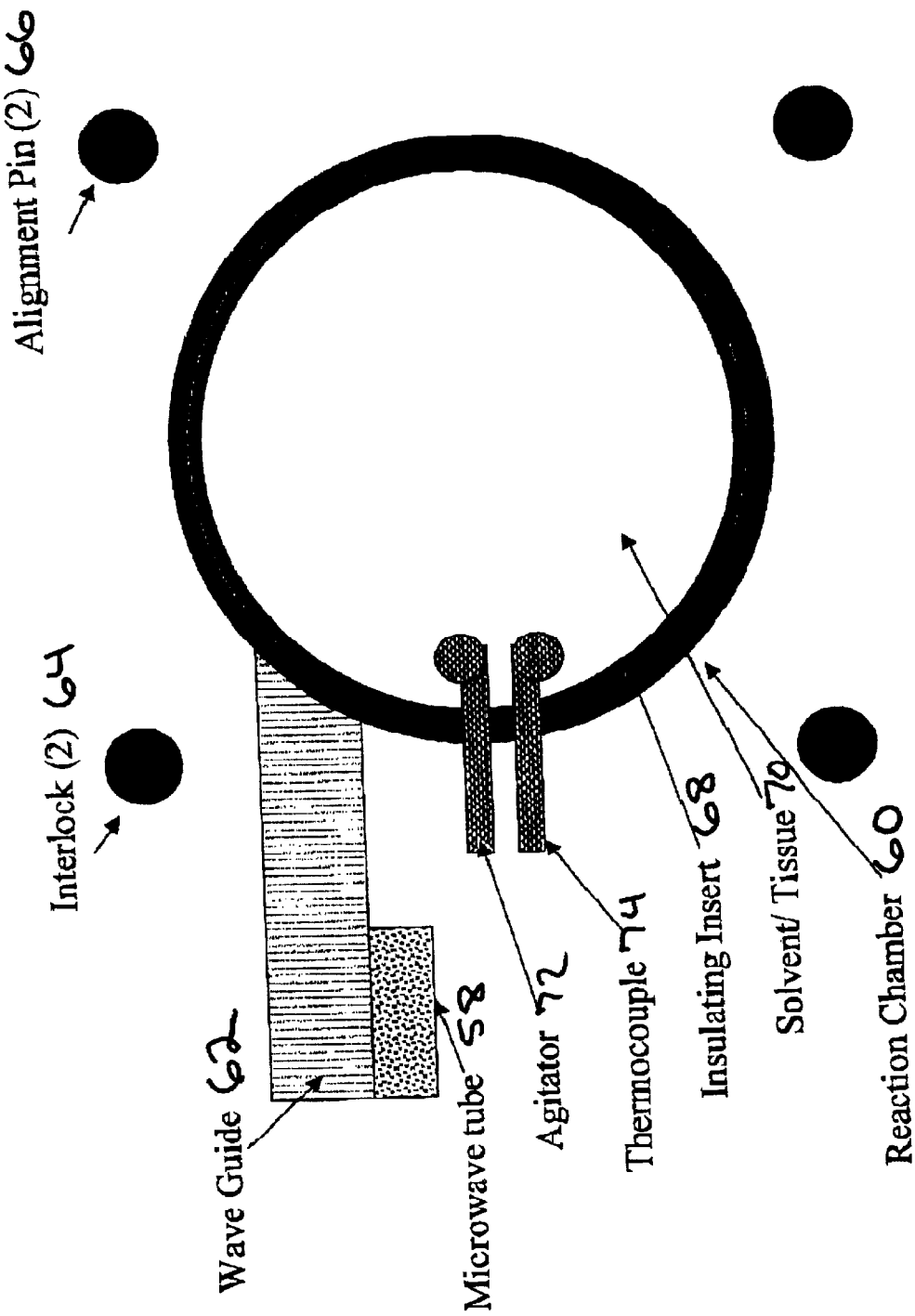

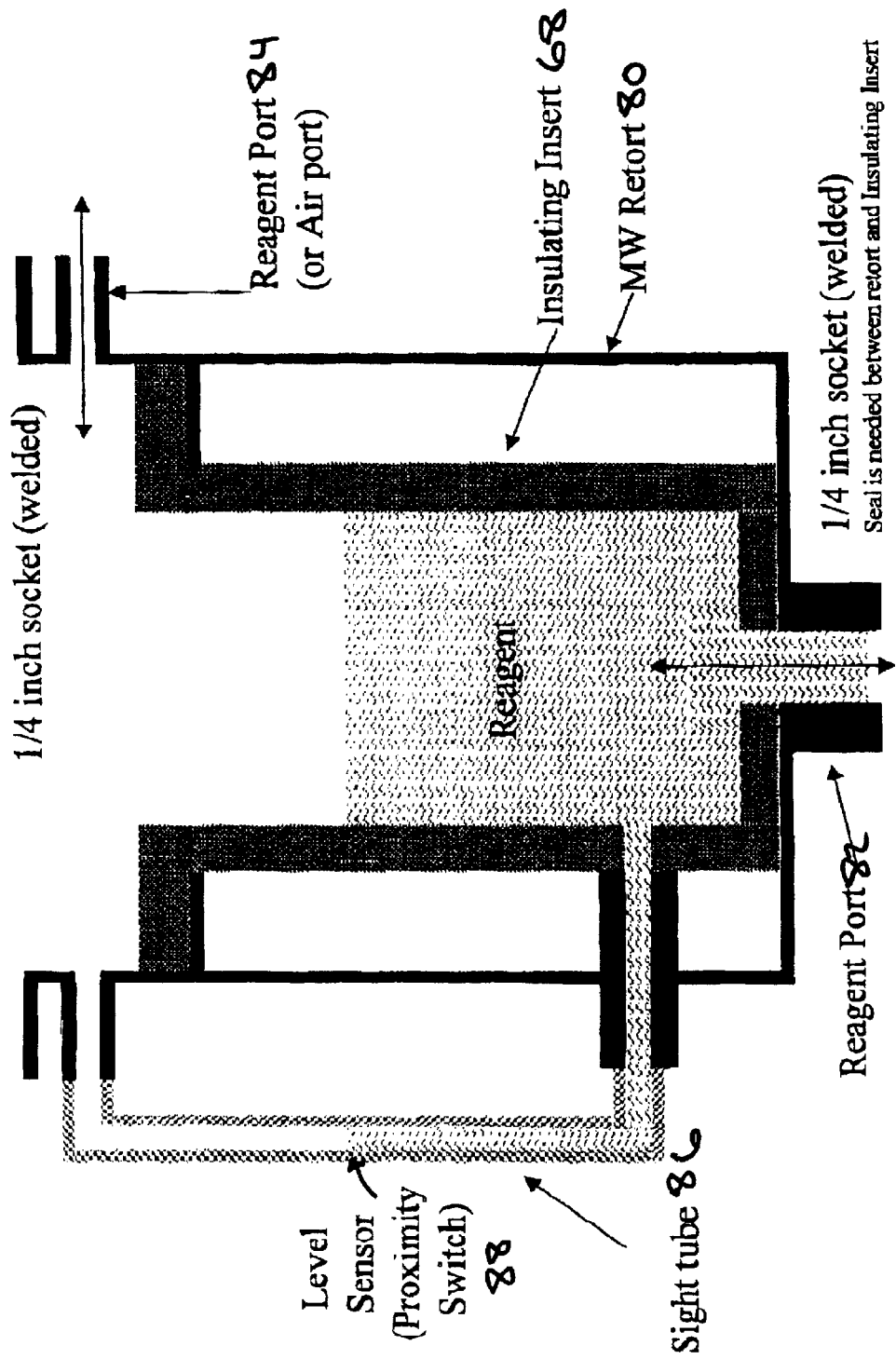

RAPID TISSUE PROCESSOR

RELATED APPLICATIONS

This application is a continuation in-part of appln. Ser. No. 09/136,292, filed Aug. 19, 1998 now U.S. Pat. No. 6,207,408, which claims the benefit of provisional Appln. No. 60/056,102, filed Aug. 20, 1997. This application also claims the benefit of provisional Appln. No. 60/170,545, filed Dec. 14, 1999.

BACKGROUND OF THE INVENTION

1. Field of the Invention

The present invention relates to the rapid, continuous flow, processing of tissue for histology, from fixation to impregnation. In particular, it relates to an automated tissue processing system that can be operated with continuous throughput and uses a sequential series of different non-aqueous chemical solutions to harden a tissue specimen and to produce a wax-impregnated tissue specimen suitable for embedding and sectioning.

2. Description of the Related Art

Conventional methods prepare tissues for histology by incubation in separate solutions of phosphate-buffered 10% formaldehyde for fixation, a series of increasing concentrations of ethanol for dehydration, and xylene for clearing tissue of dehydration agent, prior to impregnation. Because of the time required for this process, usually 8 hours or longer, it is customary to complete these separate steps—fixation, dehydration, clearing, and impregnation—overnight in automated mechanical instruments designed for those tasks (see, for example, U.S. Pat. Nos. 3,892,197; 4,141,312; and 5,049,510).

Automated tissue processors implementing such conventional processes are manufactured and sold by, for example, Shandon (HYPERCENTER and PATHCENTRE models), Miles-Sakura (TISSUE-TEK models), and Mopec-Medite (TPC15 model).

A disadvantage of the prior art is that such automated systems have not been capable of continuous throughput. Given the time required to complete tissue processing, cassettes containing tissues are loaded into the system during the day and tissue processing is completed in an overnight cycle. Thus, operation of the prior art systems did not allow tissue-containing cassettes to be processed to completion during the work day.

For example, the TISSUE-TEK vacuum infiltration processor (VIP) series requires more than eight hours for completion of processing. Baskets holding the cassettes are placed in a retort in which tissue is processed. In addition, 14 stations supply solutions of various compositions to the retort. User-programmable software controls this automated process. A rotary valve regulates the movement of solutions between the retort and the various stations; applying pressure or vacuum to the retort when the valve is open causes solution to be pumped out of or pumped into the retort, respectively. Upon completion of a processing run, the instrument automatically prompts the use for a cleaning cycle; this requirement can be overridden only if no paraffin is used. Typically, tissue specimens are batch processed according to the following program:

| | Solution | Concentration | Set Time (min) | Set Temperature | P/V ** | Agitation | Volume of Solution |
|---|---|---|---|---|---|---|---|
| 1 | Buffered formalin | 10% | 50 | 40° C. | On | On | 2.2–3.2 L |
| 2 | Buffered formalin | 10% | 50 | 40° C. | On | On | 2.2–3.2 L |
| 3 | Alcohol* | 80% | 50 | 40° C. | On | On | 2.2–3.2 L |
| 4 | Alcohol | 95% | 50 | 40° C. | On | On | 2.2–3.2 L |
| 5 | Alcohol | 95% | 50 | 40° C. | On | On | 2.2–3.2 L |
| 6 | Alcohol | 100% | 50 | 40° C. | On | On | 2.2–3.2 L |
| 7 | Alcohol | 100% | 50 | 40° C. | On | On | 2.2–3.2 L |
| 8 | Alcohol | 100% | 50 | 40° C. | On | On | 2.2–3.2 L |
| 9 | Xylene | 100% | 50 | 40° C. | On | On | 2.2–3.2 L |
| 10 | Xylene | 100% | 50 | 40° C. | On | On | 2.2–3.2 L |
| 11 | Paraffin | | 50 | 60° C. | On | On | 4 L |
| 12 | Paraffin | | 50 | 60° C. | On | On | 4 L |
| 13 | Paraffin | | 50 | 60° C. | On | On | 4 L |
| 14 | Paraffin | | 50 | 60° C. | On | On | 4 L |

**P/V (Pressure/Vacuum): agitation is provided by alternating the application of pressure and vacuum to the retort when "P/V" is On. Otherwise, when "Agitation" is On, agitation can also be provided by pumping in and then pumping out the same solution every 20 minutes.
*The alcohol used in most laboratories is a mixture of 90% ethyl, 5% methyl, and 5% isopropyl alcohol.

Typically such conventional methodology demands sending tissue specimens from the operating room, medical office or other sites, to a pathology laboratory sometime during the working day; overnight batch processing of the specimens, so that a tissue specimen suitable for blocking and sectioning is only available on the morning of the next day; and rendering a diagnosis by a pathologist based on microscopic examination of sections prepared from a blocked and sectioned specimen later on that next day (FIG. 1). This requires almost 24 hours between receipt of the specimen and delivery of the pathologist's report. Although a shortened version of the conventional method is presently practiced, it is feasible only for small biopsies. These biopsies need to be fixed for at least about 30 minutes before initiating the processing cycle. The instrument processing cycle can be programmed to last a minimum of 70 minutes, but is preferably 2 to 2½ hours.

In addition to the minimum one-day delay in giving a surgeon the benefit of a report from the pathologist, there are also problems associated with impeded work flow in the pathology laboratory necessitated by the requisite batch processing of specimens, the safety concerns that attend having instruments operating overnight, the risk of possible instrument failures and the need to monitor the instruments, and the waste of using large volumes of reagents for such processing when automated. Moreover, expensive measures are required to prevent exposure of laboratory personnel to noxious fumes and toxic substances associated with the reagents used in this process. Also, the large volumes of solvent waste and paraffin debris produced by the conventional methodology will pollute the environment if not properly disposed.

Conventional fixation and processing also cause irreversible damage (e.g., hydrolysis of a phosphodiester bond and/or deamidation) to the structure of nucleic acids (e.g., DNA, and especially RNA) that limits the application of genetic techniques for diagnosis and research. Consequently, most DNA and certainly RNA analysis require special precautions with handling of material, such as immediate freezing of fresh tissues to prevent degradation, because retrospective genetic analysis is impaired by the conventional methodology.

Histological diagnosis of a frozen section suffers from multiple disadvantages in comparison to sections prepared from paraffin blocks. U.S. Pat. No. 3,961,097 cautions that the slide prepared from a frozen section "does not possess . . . uniformity of quality;" "it is technically more difficult for serial sections of the same specimen to be examined;" "extreme caution must be exercised in cutting the specimen in order to ensure a sufficiently thin section and to avoid the possibility of damaging details of the specimen;" and all the slides must be prepared "while the tissue is in the initial frozen state" because "[i]f the tissue is thawed and refrozen for sectioning, it is severely damaged."

There is an ever present interest in expediting tissue processing and analysis for diagnostic purposes. Furthermore, recent healthcare focus has been directed to lessening the cost of various procedures including tissue processing. The costs of tissue processing are related to the time for processing and analysis of the specimens, the space required for the personnel and equipment in the laboratory, the volume of reagents (both the purchase price of the pure chemicals and the charges for discarding waste), and the number of personnel required. More importantly, patients and their physicians depend on evaluation and diagnosis by the pathologist to guide treatment. Reducing the amount of time needed to complete tissue processing would lessen the anxiety experienced during the period between obtaining the specimen and delivering the pathologist's report to the surgeon.

Others have recognized the need to shorten the time required for tissue processing, but they have made only modest improvements in the conventional methods. To accelerate tissue processing, U.S. Pat. Nos. 4,656,047, 4,839,194, and 5,244,787 use microwave energy; U.S. Pat. Nos. 3,961,097 and 5,089,288 use ultrasonic energy; and U.S. Pat. No. 5,023,187 uses infrared energy. U.S. Pat. No. 5,104,640 disclosed a non-aqueous composition of a fixative, a stabilizing agent, and a solubilizing agent that adheres a blood smear to a slide. But the aforementioned patents do not teach or suggest that the entire process of preparing diagnostic tissue slides could be accomplished in less than two hours, starting from fixation and ending with impregnation, with continuous processing of specimens.

Microwave ovens similar in design to those used in home cooking have been used to accelerate the time required for tissue processing. U.S. Pat. No. 4,656,047 claims a method of tissue processing in which at least one of the dehydrating, clearing, or impregnating steps utilizes microwave energy. Fixation may be accomplished by immersing the tissue specimen in chemical fixative and then exposing the specimen to microwave energy for a time sufficient to chemically fix the specimen. U.S. Pat. No. 4,839,194 claims a method of fixing a tissue specimen at a temperature not to exceed 40° C. in which the non-thermal effects of microwave energy are used. U.S. Pat. Nos. 4,839,194 and 5,244,787 claim a method of staining tissue specimens utilizing microwave energy.

In such conventional methods of tissue processing, the distribution of microwave energy is not uniform because of reflection and interference effects within the chamber in which the microwaves resonate and the waveguide that conducts the microwave energy from the source to the chamber. U.S. Pat. No. 4,835,354 proposes a mechanical solution utilizing a rotating platform to ensure uniform contact with the microwaves, and mixers and isolaters that disperse and absorb microwaves. U.S. Pat. No. 5,289,140 proposes a solution that utilizes a combination of microwaves of different wavelengths and/or intensities, or sources emitting microwaves of different frequencies. U.S. Pat. No. 5,796,080 discloses adjustable moderating means between the waveguide and a plurality of resonance chambers to individually control the chemical reaction in each chamber, such that the propagated mode of the microwaves in the wave-guide is not substantially changed.

We now describe a microwave unit that provides gentle uniform heating during tissue processing in a manner distinct from that disclosed in the aforementioned patents. Such operation causes minimal damage to the processed tissue, and results in a superior specimen for subsequent histologic studies by a pathologist or cell biologist. In contrast to the solutions disclosed in the patent discussed above, the microwave unit of the present invention does not use a resonance chamber which would be sensitive to the contents of the chamber. This is an important consideration when heating a region that is larger in all dimensions than about 10%–20% of the wavelength of the microwave used and the chemical compositions in the chamber change in different steps of the process. In the invention, microwave energy is distributed into the solution and tissue in such a way as to minimize interference effects. By distributing the energy, it is absorbed by the solution and tissue in one pass through the materials.

Some improvements that result from the invention are summarized here, but other improvements are described below. Convective heat losses from the reaction chamber and the evaporation rate of liquid in the reaction chamber are reduced, volatile substances are prevented from contacting electronic components and vented to protect the laboratory personnel in the vicinity of the unit, errors committed during processing by a human operator are eliminated, the power required by the unit to maintain the liquid temperature in the reaction chamber is reduced, and labor and reagent costs are reduced with this system as compared to manual operation. More subjectively, consistency in the quality of tissue specimens processed by the disclosed process is improved. Although one microwave unit may be used advantageously, multiple units may be operationally and physically linked to accelerate chemical reactions performed in batch and/or continuous mode.

SUMMARY OF THE INVENTION

It is an object of the invention to provide a microwave unit and a system for tissue processing that reduces the time required for processing and analysis, and reduces the cost thereof. The tissue processing system is capable of automation and, preferably, accepts specimens in a continuous manner. This allows conversion of existing practice to rapid response surgical pathology for the patient undergoing an operation, and may even allow point-of-care diagnosis by the pathologist in the vicinity of the operating room.

In particular, the microwave unit can provide gentle heating of tissue specimens and prevents over cooking. Uniform heating in the reaction chamber ensures specimens at different locations in the chamber are maintained at about the same temperature. Thus, both the temperature throughout the chamber and during steps of the process are kept substantially the same. A preferred configuration for the chamber is built in whispering gallery mode. Disadvantages of conventional microwave ovens (e.g., hot spots that over cook tissue and do not maintain a solution at substantially the same temperature within the chamber) are avoided by the invention.

The system for tissue processing may utilize the microwave unit as at least one module of the system. Such system may be manually operated or automated. Tissue specimens may be loaded into the system and processed either continuously and/or batchwise. Throughput may also be increased by using a plurality of individual systems arranged in parallel. Continuous processing is accessing an individual series of modules with a tissue specimen or batches thereof prior to the completion of processing without otherwise interrupting the system. The system may be adapted for use in the processes described herein and in previously filed applications; or in other histochemical reactions.

A microwave unit of the invention is comprised of (a) a source for the microwave energy, (b) a waveguide that transmits the microwave energy from the source to a reaction chamber, and (c) a reaction chamber that receives the transmitted microwave energy and processes a tissue specimen by at least initiating hardening (e.g., fixation, dehydration, or a combination thereof). The reaction chamber may contain a plurality of different tissue specimens; for example, the reaction chamber may be configured to contain a carrier or basket loaded with tissue specimens. Preferably, the interior geometry of the reaction chamber is configured to achieve uniform distribution of microwave energy and heating of its contents. Similarly, the source and the waveguide may be configured to achieve minimal energy loss during transmission of the microwave radiation. Power delivered by the microwave source, and thus the heating of the reaction chamber's contents, may be regulated by a variable current source to allow continuous variation of the power.

The microwave unit may be further comprised of any combination with or without a removable container adapted to fit within the reaction chamber; at least one temperature and/or pressure probe to monitor conditions in the reaction chamber; a closure adapted to fit the reaction chamber and to isolate the reaction chamber from the operator's surroundings (e.g., a lid attached or removable from the reaction chamber); thermal insulation to retain heat in the reaction chamber; a seal to isolate electronic components from chemicals in the reaction chamber; and control circuitry to receive input from at least one probe and/or timer, and to regulate the microwave energy emanating from the source.

In contrast to the invention, batch processing is required by the prior art because that conventional methodology may take eight hours or longer. In the prior art, specimens are loaded into an automated instrument and cannot be loaded with additional specimens until the entire instrument cycle is completed. All the tissue specimens loaded into the prior art instrument are at the same stage of processing during the entire instrument cycle.

Further advantages of and improvements due to the invention are described below.

BRIEF DESCRIPTION OF THE DRAWINGS

FIG. 1 is a flow chart showing that almost 24 hours elapse between the time a tissue specimen is obtained by a surgeon and the time a diagnosis by a pathologist can be prepared from microscopic examination of sections of the tissue.

FIG. 2 is a flow chart showing that diagnosis by a pathologist in accordance with the invention can be made available to the surgeon who provided the tissue specimen in about two hours or less.

FIG. 8A is a cutaway top view and

FIG. 8B is a cutaway side view.

FIG. 8C is a more detailed side view of the reaction chamber of the microwave unit.

DETAILED DESCRIPTION OF THE INVENTION

Figure 3:
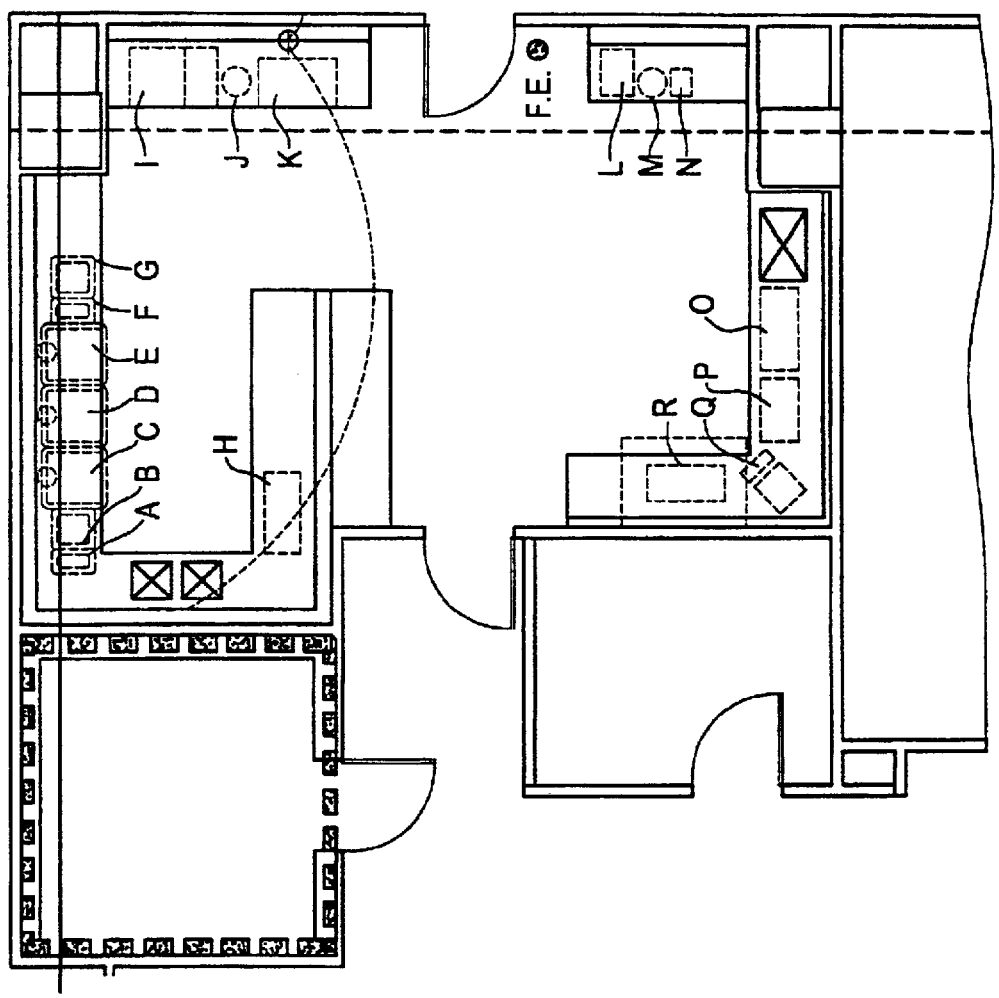
FIG. 3 is a schematic illustration of a tissue processing system that may be manually operated in batch and/or continuous mode.

The microwave unit disclosed herein may be used to advantage in conventional tissue processing, but it has been developed in the context of and may be adapted for use in the process described herein and in U.S. Appln. Ser. No. 60/056,102 and Ser. No. 09/136,292.

Over 150,000 tissue specimens have been processed by the invention (see FIG. 2 for an illustrative example). This represents about 30,000 cases per year, and an average of three specimens processed per case. The steps of fixation, dehydration, and impregnation can be performed in less than about two hours. This allows a pathologist to evaluate specimens shortly after receipt; perhaps while the patient is still in the operating or recovery room. Patient anxiety can be advantageously reduced by shortening the time required for pathological diagnosis. Rapid and continuous flow processing is accomplished by decreasing the thickness of tissue specimens, use of non-aqueous solutions composed of admixtures, solution exchange at elevated temperature and with agitation, uniform heating of tissues and solutions with microwave radiation (e.g., less than about 3° C. or 1° C. variation throughout), impregnation under vacuum pressure, or combinations thereof.

With regard to the processing and analysis of solid tissue, a tissue slice must be on the order of 3 to 6 microns to be examined under a microscope, whereas the thinnest slice of fresh tissue that can be obtained by cutting is about 1 mm with the typical slice being on the order of about 2–3 mm. In order to produce a sufficiently thin slice for microscopic examination, it is necessary to harden the tissue so that a finer slice can be obtained (e.g., by sectioning with a microtome). The present invention greatly accelerates the tissue hardening process and thereby turns the conventional overnight processing into a process which totals on the order of about 65 minutes.

We have developed a simple, safe, low cost, expeditious, and reliable process that permits preparation of impregnated tissue blocks suitable for microtome sectioning in less than two hours from the moment tissue is received in the pathology laboratory. The invention allows continuous throughput and flow of specimens, is adaptable to automation, precludes the need for formalin and xylene with their noxious fumes, allows standardization of tissue processing, and requires considerably smaller volumes of reagents than conventional methods. Either fresh or previously fixed tissues can be processed.

In addition to the reduction in time required for tissue processing, the rapid preparation of tissue by the present process is capable of preserving tissue structures and morphology that were lost with conventional methodology. Glycogen is almost always lost using the conventional methodology. Lymphatic vessels, particularly of the myometrium, collapse during conventional processing while they remain widely patent when the present invention is used.

Moreover, studies with tissues processed in accordance with the invention indicate better preservation of DNA and RNA extraction as compared to conventional processing methods. Tissues obtained in hospitals and other surgical settings can be processed for both histologic and genetic studies soon after delivery to the laboratory, and archival material may be made available for future research and other applications. Improvements may be expected in the yield of genetic material, the stability of the genetic material in archival form, the size and integrity of the genetic material, and reducing chemical modification of the genetic material in comparison to the prior art.

In the context of the invention, a "tissue specimen" is a piece of tissue that may be processed by the methods disclosed herein. It may also refer to single cells from any biological fluid (e.g., ascites, blood, pleural exudate), or cell suspensions obtained from aspiration of solid organs or lavage of body cavities. Single cells may be pelleted by sedimentation or buoyant centrifugation prior to processing. As shown in the examples, solid pieces (i.e., tissue slices) are commonly processed for histology and pathology.

By "continuous" processing, we mean accessing the system of the invention with additional tissue specimens at intervals determined by the time required to complete an individual step of the process (i.e., a few minutes) instead of the time required to complete the process (i.e., an hour to several hours). At any given time with the invention, there can be tissue specimens at different stages of processing. In other words, there can be continuous throughput and flow of specimens along the various stages of tissue processing with the invention. Continuous processing may be accomplished manually or by an automated instrument.

In one aspect of the process, a tissue specimen is fixed, dehydrated, and fat is removed (i.e., defatted). A suitable admixture for use is a non-aqueous solution comprised of fixative and dehydrating agents, preferably a ketone and an alcohol; the volume ratio of alcohol to ketone may be between about 1:10 to about 10:1 (although such extremes may change the processing time or results may be less reliable), greater than about 1:6 or about 1:3, less than about 3:1 or about 6:1, about 1:1, or any intermediate range thereof (e.g., between about 1:1 to 6:1). The tissue specimen may be incubated for a time of about 25 minutes or less, about 15 minutes or less, or about 5 minutes or less. The temperature of incubation may be between about 30° C. and about 80° C., greater than about 40° C. or about 50° C., less than about 70° C. or about 75° C., or any intermediate range thereof (e.g., between about 40° C. and 75° C.).

Another aspect of the process is fixation, dehydration, defatting, and clearing of a tissue specimen. A preferred solution is alcohol and a clearant. This step of the process may be accomplished in about 5 minutes or less.

In yet another aspect of the process, a tissue specimen is cleared and impregnated in a single solution comprised of a clearant and an impregnating agent. This step of the process may be accomplished in about 5 minutes or less. Prior to sectioning, the impregnated tissue specimen may be embedded in the impregnating agent.

A tissue specimen which has been fixed, dehydrated, and defatted may then be impregnated in a wax solution. Consistent with dehydration of the tissue specimen, the wax solution is preferably as low as possible in water content. Thus, the wax solution may be prepared prior to impregnation by heating the wax to evaporate any dissolved water and by degassing under reduced pressure. Impregnation of the tissue specimen may take place under less than atmospheric pressure and at elevated temperature to remove any solvents from the tissue specimen and to draw the wax solution into the tissue specimen. Vacuum decreases impregnation time by accelerating diffusion and reducing the evaporation temperature of any solvents that may be present in the specimen. The wax solution may comprise degassed paraffin and/or mineral oil. Impregnation of the tissue specimen may be completed in about 25 minutes or less, 20 minutes or less, or about 15 minutes or less. The wax solution may be solid at room temperature and molten above about 65° C. or about 70° C. (e.g., impregnation at a temperature between about 45° C. and about 75° C.). Prior to sectioning, the impregnated tissue specimen may be embedded in the impregnating agent to form a tissue block.

Another embodiment of the invention is processing a tissue specimen from fixation to impregnation in a series of solutions, at least some of which are admixtures performing more than one task at the same time: fixation, dehydration, removal of fat, and impregnation. The admixture may include fixative, dehydrating agent, and fat solvent (e.g., ketone and alcohol). Another solution may include fixative, dehydrating agent, fat solvent, and clearant (e.g., alcohol and xylene). Yet another solution may include a clearant and an impregnating agent (e.g., xylene and paraffin). The tissue specimen may be impregnated in a wax solution comprised of a mixture of different chain lengths (e.g., at room tempera-ture, mineral oil which is liquid and paraffin which is solid). Although many chemicals are multifunctional, preferred admixtures contain more than one chemical. Preferably, an admixture contains at least two or three different chemicals (e.g., alcohol and ketone; alcohol, ketone, and mineral oil or wax).

Processing time may be reduced by a non-aqueous admixture (e.g., fixative-dehydrating agent-fat solvent, fixative-dehydrating agent-fat solvent-clearant, clearant-impregnating agent), microwave energy as a source to achieve uniform heating within the tissue specimen, and reducing the pressure by using a vacuum source. Diffusion of the solution into the tissue specimen and chemical exchange may be promoted by mechanical agitation, heat, reduced pressure, or a combination thereof.

The above steps may be accelerated by adding an enhancer, a surfactant, or both to the solutions used in the process. The enhancer may be polyethylene glycol (PEG), mono- and dimethyleneglycol, propylene glycol, polyvinyl pyrrolidone, or the like; the polymer used may be between about 100 and about 500 average molecular weight, or about 300 molecular weight. The surfactant may be dimethyl sulfoxide (DMSO), polyoxyethylene sorbitan esters (e.g., TWEEN 80), sodium dimethyl sulfosuccinate, mild household detergents, or the like.

Fixation initiates hardening of the tissue specimen, and may preserve cell morphology by stabilizing proteins and halting cellular degradation. Without chemical fixation, endogenous enzymes will catabolize and lyse the cell, and the tissue microanatomy will be altered. The fixative may be a ketone (e.g., acetone, methyl ethyl ketone); aldehyde (e.g., acetylaldehyde, formaldehyde, glutaraldehyde, glyoxal); alcohol (e.g., methanol, ethanol, isopropanol); acetic acid; heavy metals (e.g., lead acetates and citrate, mercuric salts, chromic acid and its salts, picric acid, osmium tetroxide); or the like. Indications that fixation was inadequate can include: disassociation of tissue structures, bubbles in tissue sections, poor and irregular staining, shrunken cells, clumping of cytoplasm, condensation and less distinct nuclear chromatin, and autolysis/hemolysis of erythrocytes. Generally, fixation with acetone is accomplished on a time scale of minutes instead of hours because long exposure turns tissue brittle and causes extreme shrinkage. Further contrasting with conventional fixation using formalin, use of ketones and alcohols is believed to act as fixatives by physically stabilizing proteins (e.g., precipitation) without chemically combining with them.

Dehydration removes water from the tissue specimen to promote hardening. Replacement of water in the tissue specimen with a dehydrating agent also facilitates subsequent replacement of the dehydrating agent with material used for impregnation. This solution exchange is enhanced by using a volatile solvent for dehydration. The dehydrating agent may be low molecular weight alcohols (e.g., methanol, isopropanol, ethanol, propanol, butanol, isobutanol, ethyl butanol, amyl alcohol), ketones, dioxane, alkylene glycols, ethylene glycol, or polyalkylene glycols. Failure to dehydrate the specimen can lead to inadequate impregnation, poor ribbon formation during sectioning, clefts in tissue sections, dissociation of structures, water crystals in tissue sections, and poor staining.

Microwave radiation may also assist hardening in a physical rather than chemical manner. As noted in the discussion of chemical admixtures, the combination of physical and chemical processes may decrease processing time and/or increase specimen quality. The effect of a particular physical or chemical treatment can be determined by noting the effect on tissue processing of omitting the treatment.

Fat in the tissue specimen is removed with a solvent because fat impairs clearing and impregnation. Inadequate fat removal can result in spreading artifacts of tissue sections, wrinkling of tissue sections, and poor staining. Fat may be removed from the tissue specimen with an organic solvent such as, for example, acetone, chloroform or xylene.

Optionally, the tissue specimen is cleared. The clearant extracts solvents used for dehydrating and/or defatting from the tissue specimen if they are not miscible with the impregnating agent. The tissue may become "clear" and its opacity may be reduced due to this extraction. Examples of clearants include xylene, limonene, benzene, toluene, chloroform, petroleum ether, carbon bisulfide, carbon tetrachloride, dioxane, clove oil, or cedar oil.

Finally, once the tissue specimen is suitably fixed and dehydrated, it is hardened by impregnation with and/or embedded in an agent such as paraffin, mineral oil, non-water-soluble waxes, celloidin, polyalkylene glycols, polyethylene glycols, polyvinyl alcohols, agar, gelatin, nitrocelluloses, methacrylate resins, epoxy resins, or other plastics. Hardening of the tissue specimen with adequate preservation of cellular morphology is required prior to placing the impregnated specimen in a block and obtaining ten micron or thinner sections with a microtome knife. Preferred impregnation materials are commercial wax formulae, mixtures of waxes of different melting points (e.g., liquid mineral oil and solid paraffin), paraplast, bioloid, embedol, plastics, and the like. Paraffin has been chosen for use in the examples herein because it is inexpensive, easy to handle, and ribbon sectioning is facilitated by the coherence of structures provided by this material.

This methodology is specially suitable for tissue specimens in which cell-cell contact, tissue organization, organ structure, or a combination thereof must be preserved. With the present invention (e.g., Example 3), such a specimen is a tissue slice less than about 3 mm in its smallest dimension, about 2 mm or less, about 1.5 mm or less, or about 1 mm or less.

The tissue specimen may be fresh, partially fixed (e.g., fixation in 10% formalin for 2–3 hours), or fixed (e.g., overnight fixation in 10% formalin or any other fixative). The above process allows processing of a tissue specimen from fixation to impregnation in less than about two hours, less than about 90 minutes, less than about one hour, or less than about 45 minutes or about 30 minutes. The time required for solution in each step to reach the appropriate temperature is insignificant compared to incubation time for each step, and may be disregarded to calculate the total time for processing. In particular, small biopsies and tissues less than about 1.5 mm thick, as well as those containing little or no fat, could be processed quickly. Tissue may be transported from the operating room to the pathology laboratory in a non-aqueous solution; such a transport solution may consist of equal volumes of PEG and the non-aqueous admixture described herein.

Following impregnation, the tissue specimen can be embedded to produce a block. The agent used to embed the tissue specimen is preferably the same as the material used for impregnation, but a different impregnating agent may also be used. The blocked tissue specimen can be mounted on a microtome to produce tissue sections of between about 1 micron and about 50 microns, or between about 2 microns and about 10 microns. The tissue sections may be further processed for histochemical staining, antibody binding, in situ nucleic acid hybridization/amplification, or a combination thereof. The tissue specimens are then typically examined by microscopy, but other techniques for detecting cellular properties may be used to examine the processed tissue specimen (e.g., automated cytometry, autoradiography, electrophoresis of nucleic acid).

Fixation, dehydration, and removal of fat are required for the preparation of tissue prior to impregnation. These steps are facilitated by trimming the tissue to a suitable size prior to processing, and using cassettes which hold such tissue blocks and allow their easy transfer between solutions for fixation, dehydration, removing fat, and impregnation.

If processing of the tissue specimen is incomplete, the sections cut by the microtome knife will appear cracked or "exploded". Tissue processing is deemed a failure when one or more of the following problems is encountered: embedded tissue blocks are too soft or too hard, sections fall out or show an amount of compression different from the embedding agent, sections appear mushy, tissue ribbons fail to form or are crooked, sections crumble or tear, erythrocytes are lysed, clumping of cytoplasm, condensation of chromatin, basophilic staining of nucleoli, shrunken cells, spreading artifacts, and moth-eaten effect. Another indication of incomplete processing is the odor of organic solvent coming from the block and/or shrinkage of embedded tissue after storage.

For wax-impregnated sections on glass slides made by the present invention, the wax may be melted and removed prior to staining or immunohistochemistry. The tissue section is rehydrated and then analyzed as described below with stains or antibodies. After staining is completed or the histochemical reaction is developed, the slide may be cover-slipped and viewed under a microscope. Alternatively, the stained or antibody-decorated specimen may be studied with an instrument for cytometry. The tissue blocks may be stored for archival purposes or retrospective studies.

The present invention is compatible with preparation of nucleic acids, DNA or RNA, from processed tissues. Thus, genetic study is possible for specimens collected routinely in the clinical pathology laboratory. The combined power of these technologies will be great. Histological observations may be correlated with genetics by analyzing one section by staining or immunohistochemistry, and preparing nucleic acids from an adjacent section for genetic analysis. For example, diseased and normal regions of the same section may be compared to detect genetic differences (e.g., mutations, levels of transcription), disease progression may be characterized by comparing genetics differences in samples taken at several time points, and tumor evolution may be assessed by following the accumulation of genetic differences from primary cancer to metastasis.

Mutations may be germline and used to trace genetic predisposition of disease, or mutations may be somatic and used to determine genetic alterations in disease pathogenesis. The disease may be a metabolic or neurologic disorder, malignancy, developmental defect, or caused by an infectious agent. The present invention preserves material for genetic analysis by a simple procedure and room temperature storage.

It is envisioned that the present invention will preserve tissue that yields greater amounts of nucleic acid with a higher average molecular weight than tissues processed by conventional processes.

Many features distinguish the invention over conventional methods for tissue processing: (a) thin slicing of the tissues prior to processing; (b) continuous input of tissue specimens and continuous flow through the system; (c) elimination of water from solutions (i.e., non-aqueous solutions); (d) fixation, dehydration, fat removal, clearing, and impregnation of tissue performed with uniform heating (e.g., microwave energy); (e) admixture solutions to fix-dehydrate-remove fat, fix-dehydrate-remove fat-clear, and clear-impregnate; (f) impregnation of tissue under reduced pressure with degassed impregnating agent; (g) elimination of toxic chemicals (e.g., formaldehyde and xylenes); and (h) reduction of the volume of reagents. These features make the present process simple, practical, easily implemented for continuous throughput and flow, and amenable to automation. One or more such features may be used for tissue processing in accordance with the invention to obtain the benefits thereof.

Hematoxylin-eosin staining is commonly used for histological study and may be considered a standard for comparison by pathologists. In addition, the present process has been found to be compatible with other stains including trichrome, reticulin, mucicarmine, and elastic stains as described in general references such as Thompson (*Selected Histochemical and Histopathological Methods*, C. C. Thomas, Springfield, Ill., 1966), Sheehan and Hrapchak (*Theory and Practice of Histotechnology*, C. V. Mosby, St. Louis, Mo., 1973), and Bancroft and Stevens (*Theory and Practice of Histological Techniques*, Churchill Livingstone, New York, N.Y., 1982). Such staining procedures would take between 30 minutes and several hours to complete, although rapid staining procedures are available from Fisher Scientific that require only five minutes to accomplish.

Tissue may be obtained from an autopsy, a biopsy (e.g., endoscopic biopsy), or from surgery. For cancer surgery, the ability to provide a pathological diagnosis from a stained tissue section will provide the surgeon with information that may be used prior to the patient's departure from the operating room. For example, an indication from the pathologist that the cancer is confined to the resected tissue may allow the surgeon to be conservative in treatment and to preserve neighboring healthy tissue. Alternatively, a finding by the pathologist that cancer is not confined to a resected organ would permit more aggressive surgical treatment while the patient was still in the operating room.

Over 150,000 samples of tissue have been successfully processed by the invention, including: brain, breast, carcinoma (e.g., bowel, nasopharynx, breast, lung, stomach), cartilage, heart, kidney, liver, lymphoma, meningioma, placenta, prostate, thymus, tonsil, umbilical cord, and uterus. Mineralized tissue (e.g., bone, teeth) would require decalcification prior to processing by the present process. For example, tissue may be decalcified with a hydrochloric acid/ethylenediaminetetraacetic acid (EDTA) solution from Stephens Scientific (Allegiance Healthcare Supply, catalog no. 1209-1A) according to the manufacturer's instructions. Decalcification of large bone fragments may require several hours or even days, but bone marrow biopsies may be decalcified in about 30 minutes to about one hour. Tissue samples from almost every organ of the human body and a large number of different diseased tissues have been successfully processed.

Tissue sections processed by the present process may also be used in immunohistochemistry. The present process provides tissue specimens in which antigen is recovered and preserved, the choice of fixative may be optimized for recovery and preservation of particular antigens. Non-specific binding sites are blocked, antigen is bound by specific antibody (i.e., the primary antibody), and non-bound antibody is removed. If labeled with a probe or signal generating moiety, the primary antibody may be detected directly but it is preferred to attach the probe to a protein (e.g., a secondary antibody) that specifically binds the primary antibody. Secondary antibody may be raised against the heavy or light chain constant region of the primary antibody. This amplifies the signal generated by an antigen-antibody conjugate because each primary antibody will bind many secondary antibodies. Alternatively, amplification may occur through other specific interactions such as biotin-streptavidin. Antibody binding is performed in a small volume to reduce usage of expensive reagents and maintain a high binding rate; evaporation of this small volume is reduced by incubation in a humidity chamber. The signal generating moiety is preferably an enzyme which is not otherwise present in the tissue. For example, alkaline phosphatase and horseradish peroxidase may be attached to the secondary antibody or conjugated to streptavidin. Substrates are available for these enzymes that generate a chromogenic, fluorescent, or luminescent product that can be detected visually.

The staining pattern for antigen may be used to localize expression of the antigen in the context of cellular structures revealed by counterstaining. Antigen expression can identify cell or tissue type, developmental stage, tumor prognostic markers, degenerative metabolic processes, or infection by a pathogen.

Antigen-antibody binding may also be visualized with fluorescent, radioactive, or colloidal metal probes by epifluorescence, autoradiography, or electron microscopy. Similar probes may be used to detect nucleic acid in the tissue section by in situ hybridization to identify genetic mutations or transcripts; alternatively, the nucleic acid (DNA or RNA) may be extracted from tissue sections and analyzed directly by blotting, or amplified prior to further genetic analysis.

In accordance with an exemplary system for tissue processing provided in accordance with the present invention, a series of tissue processing stations may be provided, e.g., in a single tissue processing unit or area. By way of non-limiting example, a suitable tissue processing facility is illustrated in FIG. 3. Such a facility is suitable for manual operation of the tissue processing system, in either batch and/or continuous mode.

The first step in the process, which may be carried out at the surgical theater, pathology laboratory, or elsewhere, is to prepare a suitable tissue specimen for hardening and ultimate examination. Typically, a slice of the tissue of interest is prepared. A fine slice may be obtained for processing: about 1 mm to about 3 mm thick, about 1 mm to about 2.5 mm thick, or about 1.5 mm to about 2 mm thick. The tissue slice is placed in a tissue cassette or other holder in which the tissue is contained during subsequent processing until the hardened specimen is ready for sectioning. For ease of handling many cassettes, the cassettes may be placed in a carrier or basket. The cassette or holder is next placed in a first solution provided in accordance with the invention.

Figure 4:
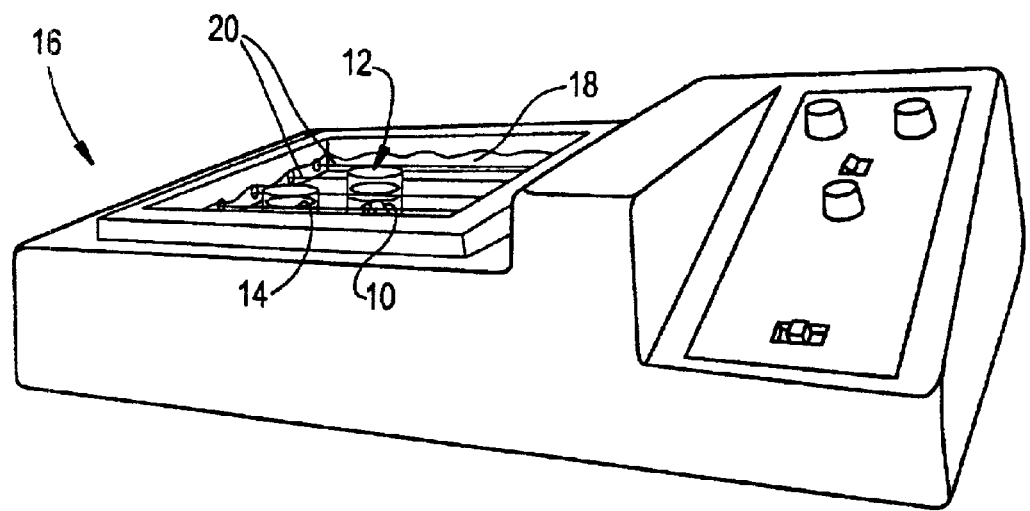
FIG. 4 shows a shaker bath, which does not provide either microwave heating or vacuum, for use in a manually-operated tissue processing system.

By way of example, the cassette or holder 10 may be placed in a Pyrex beaker 12, having the first solution 14 therein, by itself or in batches together with a limited number of other, similar tissue cassettes or holders. Processing may be manually processed in a substantially continuous manner. With reference to FIG. 4, the beaker 12 is then placed in a shaker bath 16 for gently agitating and heating the same. We have used a LAB-LINE/DUBNOFF incubator-shaker bath (B in FIG. 3) for this purpose. Rather than water, as it is our goal to minimize moisture to which the tissue specimens are exposed and, in fact, ultimately to dehydrate the same, we have provided glycerin as the temperature conducting fluid 18 in the shaker bath 16. Glycerin has the advantage that it is an effective conductor of thermal energy, but it does not evaporate. Evaporation would undesirably increase the moisture of the environment in which the tissue is processed, and would require periodic replenishment. Because the glycerin neither needs replacement nor adds moisture to the environment, it is most preferred. For this stage of the process, the tissue specimen (in cassette or holder 10) is disposed in the first solution, in the shaker bath 18 for about 3 minutes to about 15 minutes.

Supplemental agitation is desirably also provided during the shaker bath step. An external pump (A in FIG. 3) is provided with a tube (not shown) therefrom inserted into the solution beaker 12 or other receptacle for bubbling and thus agitating its contents. An aeration diffusion nozzle or plate may be provided to provide for more uniform solution agitation as deemed necessary or desirable.

To ensure that the tissue cassette or holder 10 and first solution containing beakers 12 remain upright and in a desired disposition, we have modified the conventional shaker-bath to provide transverse wires or stays 20, e.g., four wires, defining, e.g., five longitudinal channels in which tissue cassette- or holder-containing beakers 12 may be disposed. Thus, for example, specimen-containing beakers 12 may be regularly added to the shaker bath 18 and sufficiently processed tissue specimens removed in turn therefrom for further processing as described below, by adding new specimens on the left end of the shaker bath and removing sufficiently processed specimens from the right end thereof.

A tissue cassette or holder 10 is exposed to a series of fluids while simultaneously being agitated and subjected to microwave radiation. In one embodiment, three microwave units are provided, as shown at (C, D and E in FIG. 3), each having a different solution in which the tissue cassette or holder is submerged for a prescribed period. In the alternative, a single source of microwave energy could be provided if a waveguide transmits the microwave energy to the different solutions or there is a sequential transfer of the different solutions. A waveguide would require more complex manufacture and, while for a single tissue specimen such solution placement and replacement would not significantly increase the duration of the tissue processing cycle, it can be appreciated that the use of a single microwave unit that receives multiple solutions may hinder the continuity of the process with respect to subsequent specimens. Indeed, where a series of microwave units are provided, as a given tissue specimen is moved from one microwave to the next having the next solution, a subsequent tissue specimen can then be received in the first microwave unit. Thus, providing a microwave unit for each of the respective solutions means that a subsequent tissue specimen need not be held while all microwave processing steps of the proceeding specimen have been completed. It is to be understood, however, that with the noted hindrance of continuity, the three microwave units illustrated could be reduced to two or even one. Likewise, other steps in the process may be combined or sub-combined as deemed necessary or desirable from a balance of process continuity versus a potential reduction in manpower, equipment, space requirements, etc. An exemplary such more compact unit is discussed in greater detail below, with reference to FIG. 7.

Figure 5:
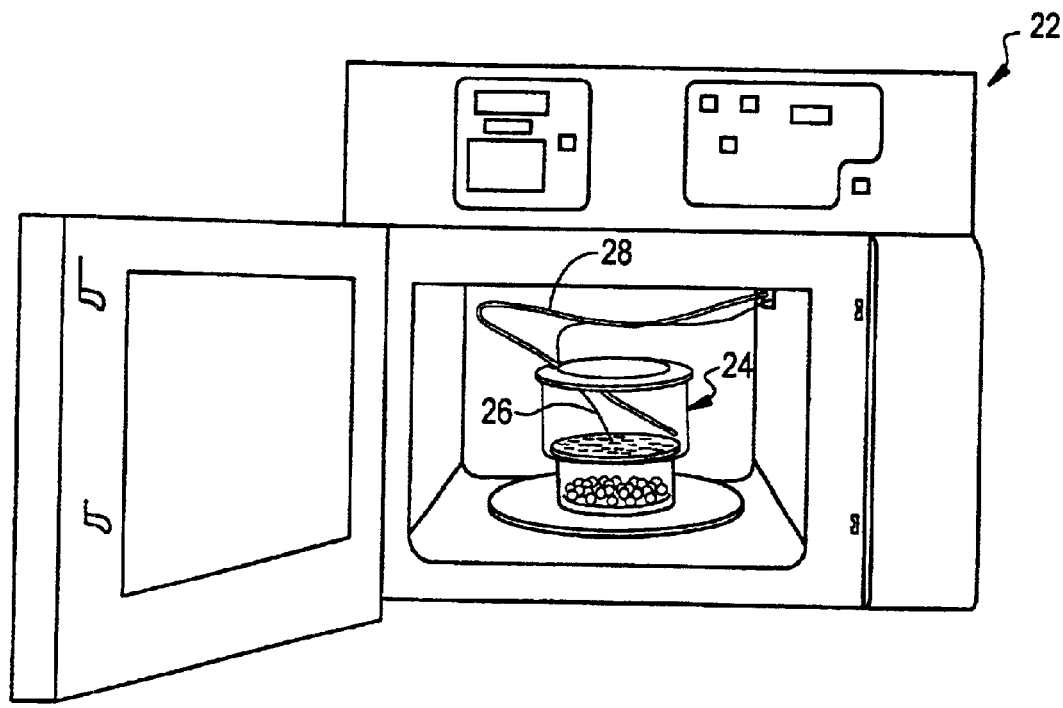
FIG. 5 shows a conventional microwave oven provided for use in a manually-operated tissue processing system.

An exemplary microwave unit 22 for tissue processing is illustrated in FIG. 5. For applying microwave radiation, we have used laboratory microwave ovens obtained from Energy Beam Sciences, Inc. We have used two microwave processor models, H-2800 and H-2500, either model or another similar such system could be used. By way of example, a Pyrex beaker or other microwave transparent fluid receptacle 24 is utilized to hold respectively second, third and fourth solutions provided in accordance with the invention in each of the three microwave units (FIG. 3). A temperature probe 26 is placed in the solution to ensure that the temperature of the respective bath is within the desired range. Moreover, to provide for agitation which accelerates tissue processing, aeration is provided. The microwave units we have used include a tube 28 for aeration. A single tube may be inserted into the bath, but for more uniform and complete agitation, a diffusion plate or nozzle head (not shown) in cooperation with the gas tube 28 for diffusing the agitating bubbles, e.g., across a substantial portion of the diameter of the solution receptacle for uniform agitation of the entire volume of solution. Such diffusion plates and nozzles are well known and can be provided, e.g., at the base of the solution receptacle. Agitation may also be provided by pumping solution into and out of the receptacle (e.g., circulating the solution through the receptacle) or using P/V cycles (e.g., 10 to 30 seconds spent under pressure, reduced to a partial vacuum, and under pressure again).

Conventionally, paraffin is degassed as a part of the tissue processing procedure. Degassing removes organic solvents from the paraffin. To enhance this process and to reuse the paraffin in the system, we propose continuous degassing. This is accomplished by maintaining the vacuum within the covered Pyrex dessicator jar 32 at 640 mm Hg.

Figure 6:
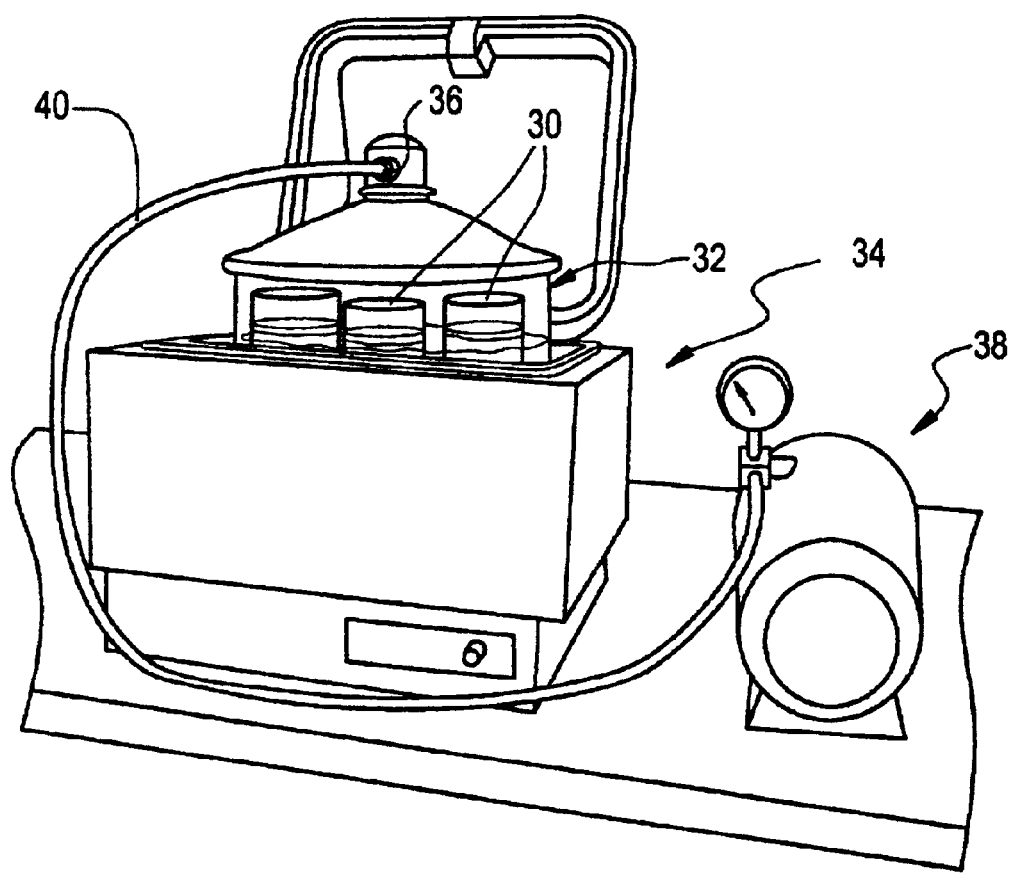
FIG. 6 shows a paraffin bath provided for use in a manually-operated tissue processing system.

Following the three sequential steps employing microwave radiation, the tissue cassette(s) or holder(s) are placed in a paraffin bath (J in FIG. 3). With reference to FIG. 6, we provide a paraffin bath comprising three paraffin bath stations (beakers) 30 provided within a covered jar 32. For the purpose of temperature control, the jar 32 is placed in, e.g., a Poly Science brand water bath 34 at (G in FIG. 3). By applying grease or the like to the internal edges of the flanges on both the lid and jar, an airtight coupling can be provided between the lid and jar and thus a vacuum can be pulled through a tooled hose connector 36 provided in the lid. Suitable such covered jars are available from Fisher Scientific (model 01-092-25). To create a vacuum within the covered jar 32, a conventional pressure/vacuum pump 38 (F in FIG. 3) is coupled to a tube 40 that is in turn coupled to connector 36. A suitable such power operated pump is available from Fisher Scientific and a pressure of about 100 psi max.

Next the tissue specimen must be embedded. For that purpose, we use a conventional TISSUE-TEK embedding console system (I in FIG. 3) available from Miles-Sakura, e.g., Model No. 4708.

The embedded tissue specimen is then cut in a conventional manner with a microtome (L in FIG. 3) and floated (M in FIG. 3) for placement, we use the Leitz 1512 microtome, and the Lipshaw electric tissue float Model 375. A hot plate is provided (N in FIG. 3).

After the slice is placed on the slide, the slide is heated to melt the paraffin and adhere the sections to the glass. We have used the Isotemp Oven 300 series available from Fisher (K in FIG. 3).

Next the slides are stained. To accelerate the staining process, we propose to use an automated stainer (O in FIG. 3) to reduce the number of personnel and time required. A non-continuous process could use the Miles-Sakura diversified stainer DRS-601 which stains slides in batches; alternatively, a continuous process could use a Leica autostainer XL which contains a dewaxing stage so that a separate incubation step in an oven may be omitted. An immunohistochemical (IHC) stainer (P in FIG. 3) and IHC controls (Q in FIG. 3) are also shown. The fixed and stained tissue specimen is then covered, e.g., with the TISSUE-TEK coverslipper, Model No. 4764 (R in FIG. 3).

As described above, the system for carrying out the dehydration and impregnation in accordance with the present process can be a series of discrete units. In the alternative, as also noted above, one or more steps can be carried out in a single processing component or unit. The number of units provided and the steps carried out by each unit affects the continuity of the tissue processing system and the time required for completion. Thus, in low volume environments, a single unit for carrying out a plurality of the tissue processing steps may be advantageous and will not significantly affect continuity of processing. In higher volume environments, a tissue processing system may be comprised of two or more units or a parallel series of units.

Figure 7:
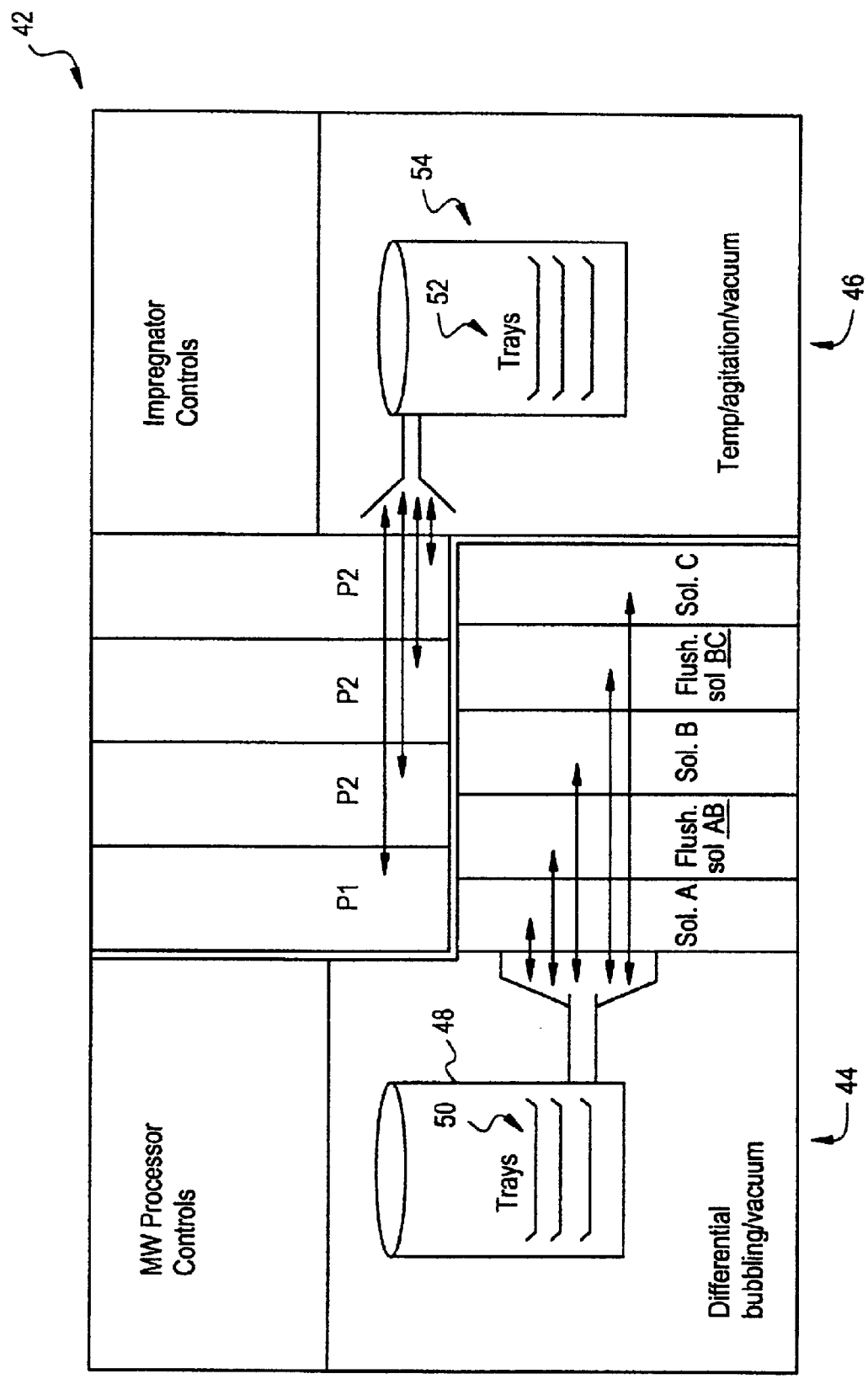
FIG. 7 is a schematic illustration of a tissue processing system that is automated, and may be operated in batch and/or continuous mode.

An exemplary tissue processing system 42 is illustrated in FIG. 7. The system 42 includes two subunits; a microwave unit 44 and an impregnator unit 46. The microwave unit 44 is provided for sequentially submerging the tissue being processed in solution A, solution B, and solution C, in each instance agitating the solution and exposing the tissue to microwave energy. Thus, in the illustrated embodiment, a vessel 48 is provided for receiving, e.g., one or more tray carriers 50 on which one or more tissue cassettes 10 may be placed. The vessel 48 is fluidly coupled to a source of each of the solutions for tissue dehydration. Thus, once the tissue cassette(s) are placed on the respective tray carrier(s) 50, solution A is conducted to the vessel 48 and microwave energy is applied thereto simultaneous with agitation via, for example, an aeration tube (not shown in FIG. 7). Agitation may be provided with a mechanical device that causes bubbling in, shaking or vibration of, or transfer of ultrasound energy into the solution. Alternatively, agitation may be provided by P/V cycles or circulation using a pump. After a sufficient time of exposure has passed, solution A is drained and the tissue cassettes are preferably flushed either with solution B or with a combination of solution A and solution B so as to substantially eliminate residual solution A. Solution B is then fed to the vessel 48, whereupon microwave energy and agitation are again applied for a prescribed period. At the conclusion of administration of solution B, solution B is returned to a storage vessel therefor and the tissue specimens are flushed either with solution C or a combination of solution B and solution C. Thereafter, solution C is fed to the vessel 48, agitation and microwave energy are applied, and ultimately solution C is drained. Transfer of different solutions into the vessel 48 can be facilitated by using the same number of dedicated storage vessels, a pump to move fluid in a tube or pipe between storage and reaction vessels, and a multi-position rotary valve to connect the different storage vessels to the reaction vessel using a common tube or pipe. The tissue specimens are then ready for impregnation.

In the illustrated embodiment, impregnation is carried out in a second impregnator unit 46 of the tissue processing system. This allows impregnation to be carried out while a subsequent tissue specimen(s) are subject to microwave energy application. If a single unit is provided, then the vessel used for microwave processing can be used for impregnation however the microwave energy would not be applied thereto during the impregnation steps.

In accordance with the proposed impregnation process, a series of paraffin solutions, e.g., three or four, are applied to the tissue cassettes disposed, e.g., on suitable tray carriers 52 in a vessel 54, to provide sequential paraffin baths to effect the impregnation of the tissue specimen as a final step in the tissue preparation process. In the impregnator unit 46, the tissue specimens are placed under a vacuum at a controlled elevated temperature. Agitation may be provided during this step with a mechanical device that causes bubbling in, shaking or vibration of, or transfer of ultrasound energy into the solution. Alternatively, a pump may be used for agitation using P/V cycles or circulating the solution.

Here, the tray carrier may be transferred between vessels manually, or by an armature or track conveyance (not shown in FIG. 7). Movement of the tissue specimens can be minimized by filling the vessel containing a stationary carrier with different solutions and then draining the vessel between changes of solution. The remaining embedding, etc. steps of slide preparation are carried as outlined above with reference to FIG. 3.

The microwave unit provides gentle heating of a tissue specimen while preventing its over cooking, and uniform heating in the reaction chamber which to ensure specimens at different locations in the chamber are maintained at about the same temperature. Over cooking is defined as a change in the histologic structure of the tissue specimen because the microwave field is too intense. Microwaves can heat the tissue specimen better than the surrounding solution; this effect is minimized by allowing sufficient time for the heat to be dissipated from the tissue specimen into the surroundings.

A microwave unit of the invention is comprised of (a) a source of the microwave energy (e.g., magnetron, klystron, traveling wave tube), (b) a waveguide that transmits the microwave energy from the source to a reaction chamber, its dimensions and shape being adapted for this purpose, and (c) a reaction chamber that receives the transmitted microwave energy and is adapted to process a tissue specimen by at least chemical fixation, dehydration, and defatting. The reaction chamber may contain a plurality of different tissue specimens. Preferably, the interior geometry of the reaction chamber is configured to achieve uniform distribution of microwave energy and heating of its contents. Uniformity is achieved primarily by consideration of two factors.

First, the circumference of the reaction chamber is made to be an integral number of half wavelengths of the microwave radiation in the chamber. With proper arrangement of the waveguide entrance into the reaction chamber, a mode will be excited that will propagate around the exterior wall. This type of mode is characterized by the microwave field being predominantly near the exterior wall. A similar phenomenon occurs in acoustics where sound waves travel very efficiently next to solid walls. These types of modes are referred to as whispering gallery modes.

A second consideration is the radial distance between the boundary of solution in the reaction chamber and its wall. The optimum spacing is determined empirically by changing that spacing. If the spacing is too narrow, the microwave radiation is absorbed primarily near the waveguide entrance to the reaction chamber. If the spacing is too wide, the reaction chamber becomes a resonant cavity and is sensitive to the amount of non-aqueous solution and solids (e.g., tissue specimens, cassettes, and basket) therein. With the proper spacing, efficient heating of the solution and solids is achieved over an extensive range of heights of the contents as measured by a level sensor outside the reaction chamber (i.e., volumes therein). As little as 10% of the fill height (i.e., total volume) still provides efficient heating of the contents.

Similarly, the source and the waveguide are configured to achieve minimal energy loss during transmission of the microwave radiation. The microwave unit is configured with a waveguide to have no more than about 2% energy loss from the source to the reaction chamber. A higher energy loss would require the use of expensive shielding and other protection devices for the source of the microwave energy.

Heating may be controlled by cycling power on-off in cycles of about 10 seconds to about 25 seconds because a minimum time is required by the heating characteristics of the cathode of the microwave source. But this may burn the tissue, so heating may be controlled through a variable current source to allow continuous variation in the power delivered by the microwave source to the reaction chamber. Such burning or over cooking is typified by homogeneous staining of tissue structures without distinguishing cellular features.

The microwave unit may be further comprised of any combination of a removable container adapted to fit in the reaction chamber and to receive at least one tissue specimen (e.g., a basket); at least one temperature and/or pressure probe to monitor conditions in the reaction chamber; one or more energy probes to monitor microwave energy being sent by the source, transmitted through the waveguide, and/or received by the reaction chamber; a closure adapted to fit the reaction chamber and to isolate the reaction chamber from the operator's surroundings; thermal insulation to retain heat in the reaction chamber; shielding to isolate electronic components from chemicals in the reaction chamber; and control circuitry to receive input from at least one probe or timer and thereby regulate at least one of the microwave energy from the source, transmitted through the waveguide, and/or received in the reaction chamber.

Characteristics of the materials used for the seal are the ability to hermetically isolate the reaction chamber from the environment, substantial transparency to microwave radiation, malleability to ensure a tight fit which conforms to the closure, and chemical resistance to solutions of the process. Modifying the reaction chamber with (a) a closure and a hermetic seal to reduce evaporation and (b) thermal insulation can reduce the power required to operate the microwave unit by two- or three-fold.

Figure 8:
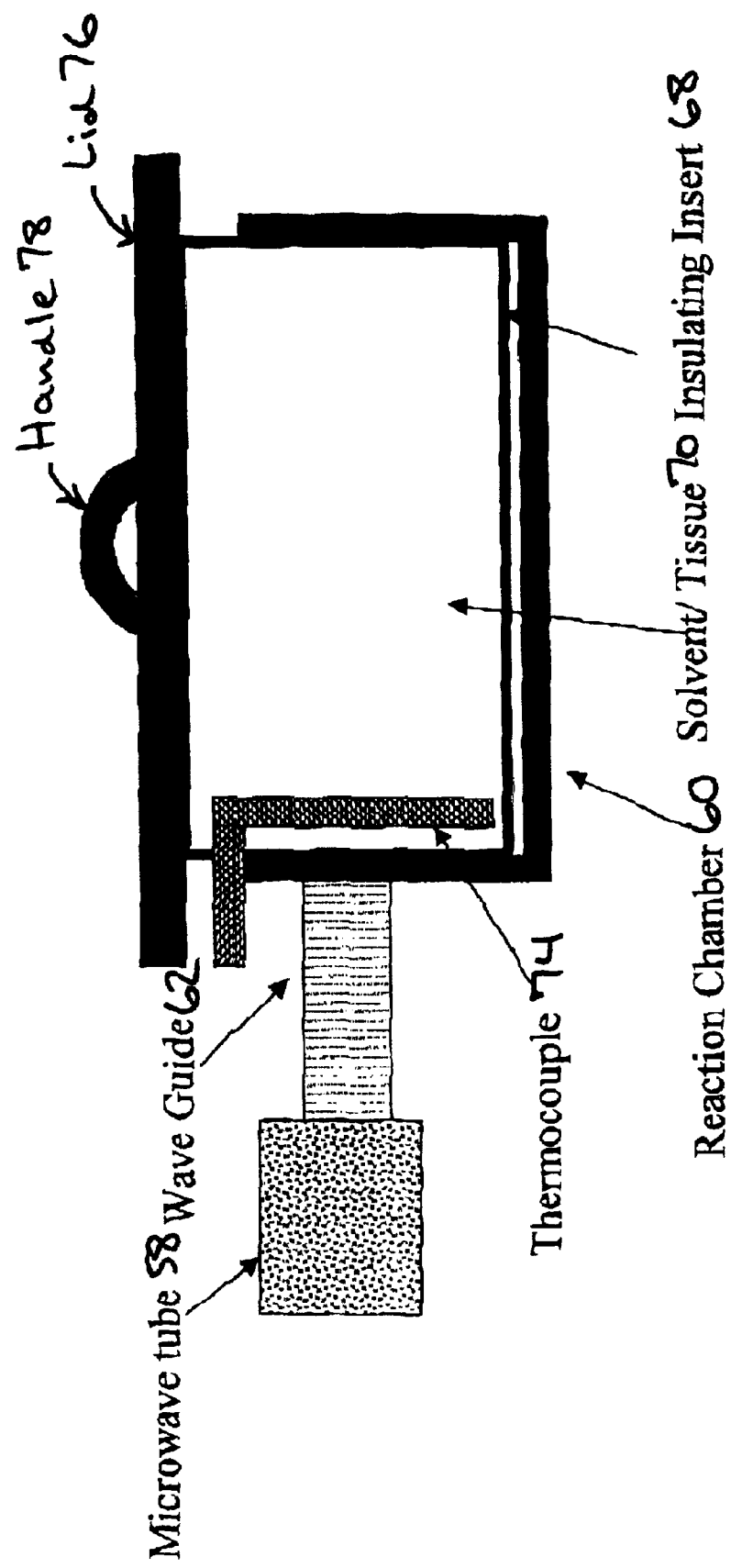
FIG. 8 is shows a microwave unit of the invention.

FIG. 8A shows a cutaway top view and FIG. 8B shows a cutaway side view of an exemplary microwave unit. Microwave energy is transferred from the microwave tube 58 to the reaction chamber 60 by the waveguide 62. Interlocks 64 ensure that the microwave unit will not operate while open and alignment pins 66 ensure that the unit is closed. An insulating insert 68 surrounds the contents 70 of the reaction chamber 60 to reduce heat loss. An agitator 72 and a thermocouple 74 is shown projecting into the reaction chamber 60. The lid 76 must be removed (e.g., by a robot arm lifting the handle 78) prior to grabbing a basket containing tissue specimens (not shown) and placing it into or taking it out of the reaction chamber 60.

A more detailed view of the reaction chamber 60 of the exemplary microwave unit is shown in FIG. 8C. The microwave unit is alternatively called a MW retort 80 because the reaction chamber 60 is isolated from the environment, but a vacuum is not required for hardening the tissue specimen. Reagent ports 82 may be used to transfer solutions into and out of the reaction chamber 60, or may be used to as an air port 84. A welded ¼-inch socket provides a seal between the insulating insert 68 and the MW retort 80. The solution level can be visualized through an external sight tube 86 connected to the interior of the reaction chamber 60. A proximity switch 88 serves as a level sensor.

Figure 9:
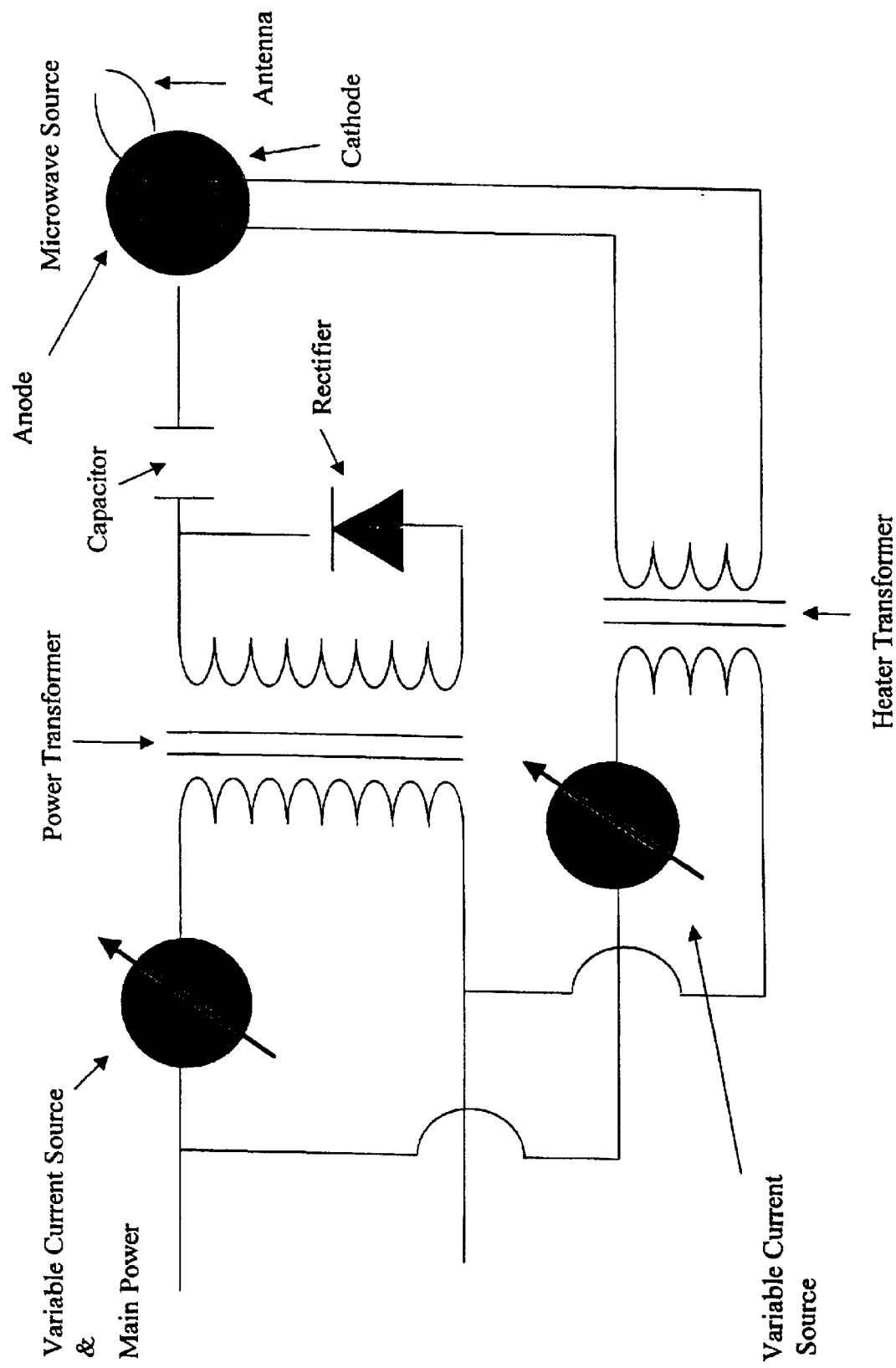
FIG. 9 shows electrical components of a microwave unit of the invention.
Figure 10:
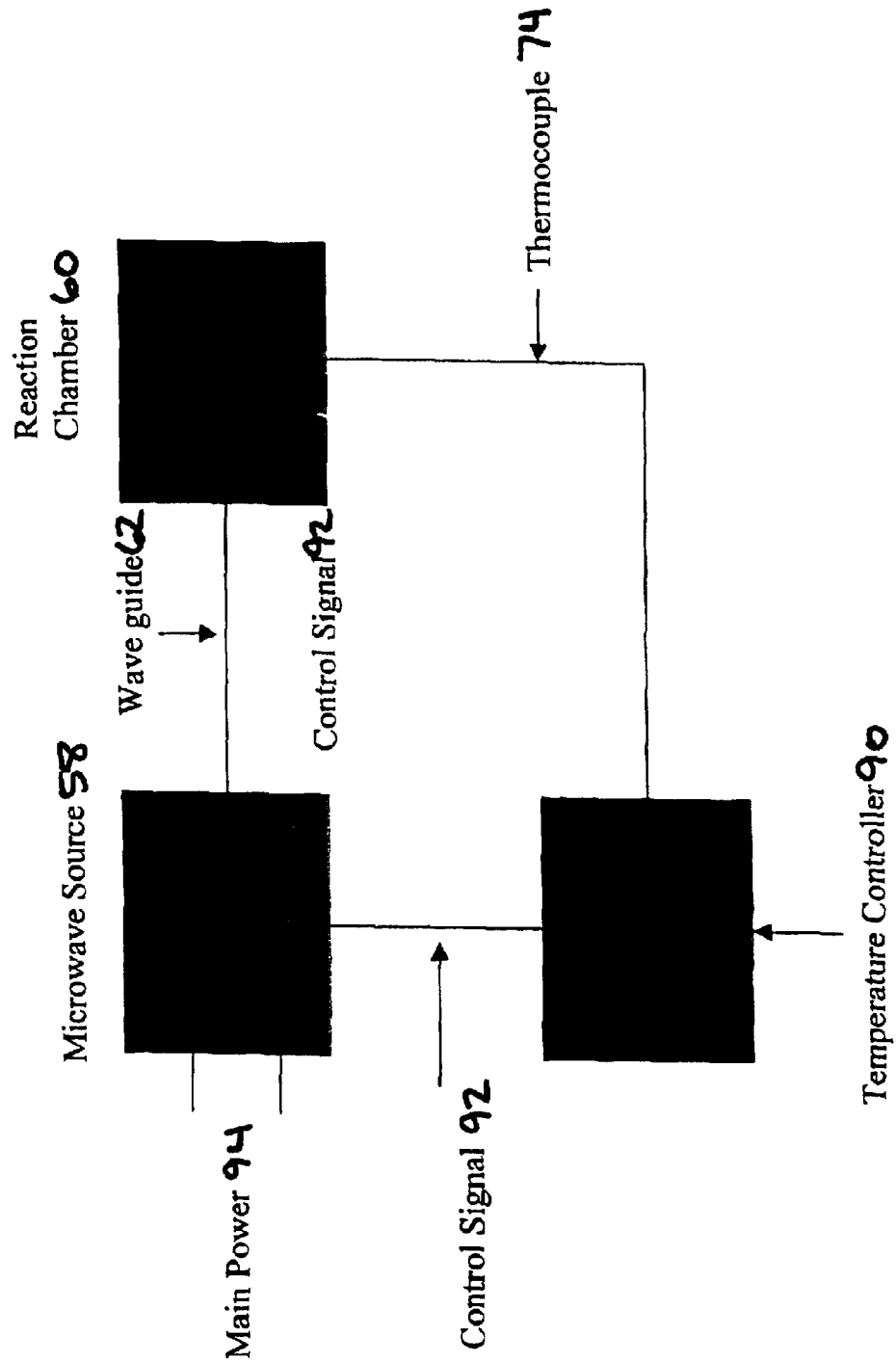
FIG. 10 is a block diagram of the control features of a microwave unit of the invention.

Electrical components of the exemplary microwave unit are shown in FIG. 9. Control of the temperature of the contents of the reaction chamber 60 is shown in FIG. 10. The temperature controller 90 is programmed with the desired temperature. A control signal 92 is sent to the microwave unit to apply power 94 to the microwave source 58, which microwave energy is transmitted by the waveguide 62 to the reaction chamber 60. The thermocouple 74 senses the temperature of the contents of the reaction chamber 60 and is fed back to the temperature controller 90. An algorithm or other program in the temperature controller 90 then adjusts the control signal 92 to make the sensed temperature approximately equal to the desired temperature.

The system for tissue processing may be comprised of a physically linked series of modules (e.g., reaction chambers with or without an operably linked microwave unit) to accomplish a combination of fixation, dehydration, defatting, clearing, and/or impregnation of a tissue specimen. The system may be comprised of one module or a plurality of them. Each module would constitute a part of the entire processing cycle, but an individual module may accomplish more than one of the steps of tissue processing (i.e., fixation, dehydration, defatting, clearing, and impregnation) because of the chemical composition contained therein. A recorder may be included to receive measurements of reaction conditions in at least one module and other performance characteristics of the system (e.g., amount of chemical in a module, time spent by a tissue specimen within a module or in contact with a chemical), and to store the measurements for retrieval by the operator.

The modules may occupy the same space and/or the tissue specimen may remain stationary. Microwave or thermal energy may be regulated and transmitted into the same space, or onto the stationary tissue specimen at different times in the process. Chemical solutions and/or vapors may be moved into or out of the same space, or brought into or out of contact with the stationary tissue specimen. Preferred is minimizing space requirements for the system by using one or two reaction chambers, and transporting the different chemical compositions into a reaction chamber by tubing or piping from separate storage and/or waste chambers. A controller can receive input from the reaction chamber and/or from timing that part of the processing cycle, and thereby regulate the transport of the different chemical compositions.

Alternatively, a plurality of modules containing at least four, five, or six different chemical compositions and to have at least one armature or track conveyance to move the tissue specimens among the modules may be provided. Thus, the system may comprise at least one, two, three, or four microwave units. In some embodiments, if a tissue specimen is transferred from one chemical composition to another with the same chemical composition, it may be possible to combine parts of the processing cycle into the same module with an exchange of the chemical composition therein. Thus, certain parts of the processing cycle may be combined and the number of different modules that are required could be reduced. Plumbing for fluid transfer may be simplified as compared to other embodiments previously described because the chemical composition may remain in the reaction chamber during the entire processing cycle and be moved into the reaction chamber only at the initiation of the cycle in a filling step, or out of the reaction chamber at the termination of the cycle in an emptying step. The number of modules may also be decreased to one or two (e.g., only one microwave unit and one impregnation unit) by using storage chambers in fluid communication with the reaction chamber and that are comprised of the different chemical compositions, and moving them into and out of the appropriate reaction chamber as needed. For example, pumps and multi-position rotary valves may be used to control fluid movement between reservoir and reaction chamber by pumping. Controller circuitry may also be simplified if movement between modules occurs in an integral multiple of a common block of time. Movement of the tissue specimen may be controlled by a program stored in memory such that the carrier or basket loaded with tissue specimens encounters modules in a particular order for set incubation times. The number of different modules, some of which may contain the same chemical composition, may be at least any integer from four to ten. Two, three, or four lines of modules may be arranged for parallel processing.

Figure 11:
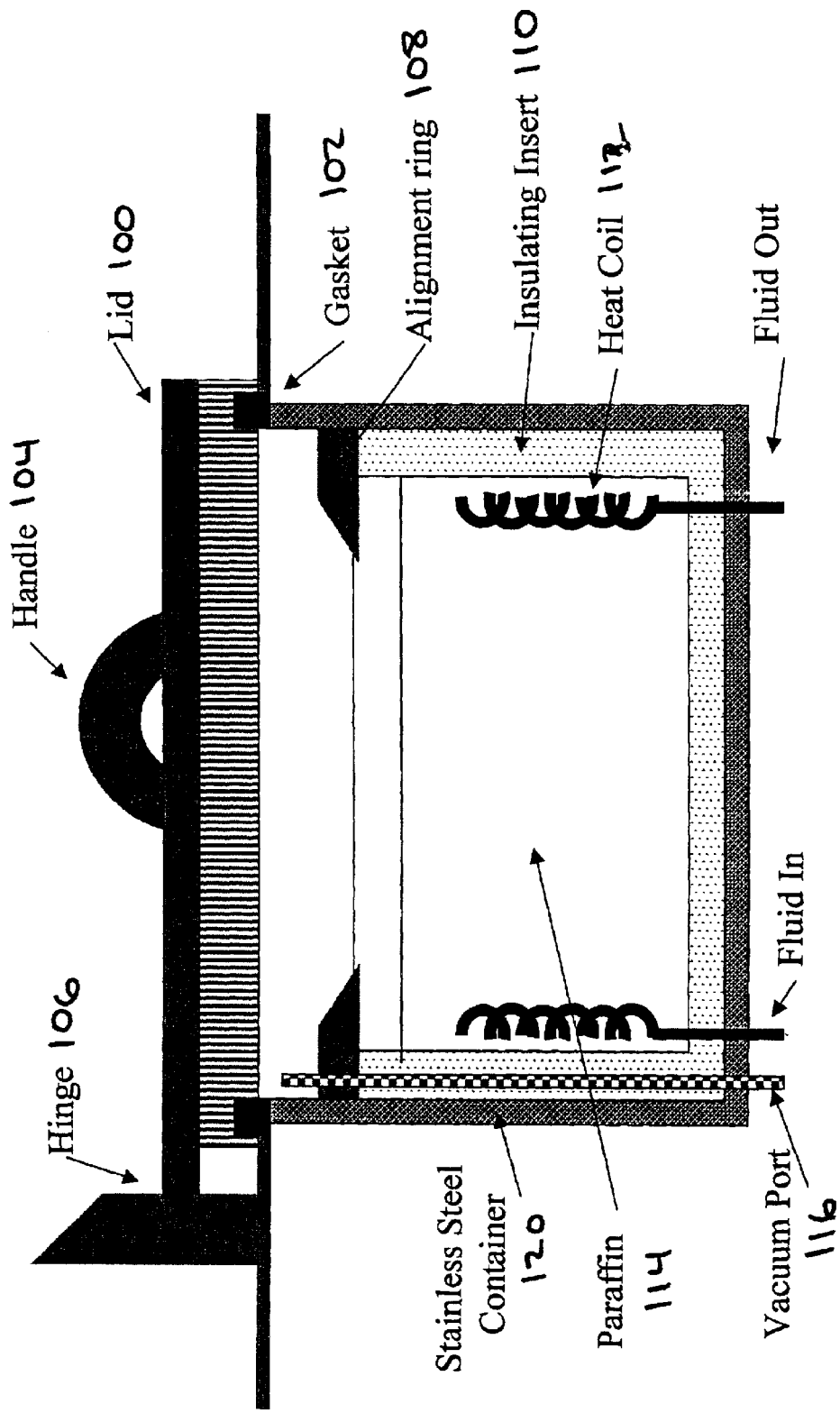
FIG. 11 shows an impregnator unit of the invention.

An exemplary impregnator unit is illustrated in FIG. 11 with a hot fluid (e.g., water) passed through the heating coil 112 to maintain the impregnating agent 114 as a liquid. Radiant heat may be provided by such coil within the interior (e.g., heating coil 112) of the reaction chamber 120 or an electrical wire wrapping its exterior (not shown). A lid 100 and gasket 102 covers the reaction chamber 120 and is displaced using the handle 104 before a basket (not shown) containing tissue specimens is grabbed. Here, a hinge 106 shows how the lid 100 is attached to the reaction chamber 120. Stainless steel may be used as the exterior surface of the impregnator unit. An alignment ring 108 over an insulating insert 110 ensures proper placement of the basket into the reaction chamber 120. The insulating insert 110 (e.g., DELRIN or other plastic material) reduces heat loss during impregnation of the tissue specimen. Reducing the pressure within the reaction chamber 120 using the vacuum port 116 hastens impregnation. The lid 100 and gasket 102 maintains the vacuum within the reaction chamber 120 after its evacuation. During transfer, the temperature of the contents of the reaction chamber 120 of the impregnator unit is maintained within about 2° C.

Either transferring different solutions into and out of the reaction chamber or transferring the basket among reaction chambers containing different solutions may effect changes in reaction steps. Holding the basket above the interior of the reaction chamber for about 10 seconds allows excess solution to drain back through one or more openings in the bottom and/or sides before the basket is transferred. Thus, the sequence in which the basket is transferred among reaction chambers, each containing a particular composition of tissue processing chemicals, and the time the basket is incubated in each reaction chamber will dictate the series of chemical reactions necessary to accomplish the process according to the invention.

The lid can be removed; the gasket can be attached to the lid and moved with it. This process of removing the lid and gasket is performed for both the reaction chamber which initially contains the tissue specimens and the next reaction chamber into which the tissue specimens will be subsequently transferred. The basket is then removed, allows solution to drain from the basket and any cassettes which may be contained therein back into the reaction chamber for about 10 seconds, and transfers the basket to the reaction chamber containing the next chemical solution in the process. Finally, the lids and gaskets are replaced. The total time for such a transfer is about one minute.

For tissue processing, a plurality of modules containing at least four, five, or six different chemical compositions and to have at least one armature or track conveyance to move the tissue specimens among the modules may be used. The system will may be comprised of at least one, two, or three microwave units. In preferred embodiments of the invention, if a tissue specimen is transferred from one chemical composition to another with the same chemical composition, it may be possible to combine these parts of the processing cycle into the same module with an exchange of the chemical composition therein. Thus, certain parts of the processing cycle may be combined and the number of different modules that are required could be reduced. Plumbing may be simplified as because, in many of the envisioned embodiments, the chemical composition may remain in the reaction chamber during the entire processing cycle and be moved into the reaction chamber only at the initiation of the cycle in a filling step, or out of the reaction chamber at the termination of the cycle in a emptying step. Controller circuitry may also be simplified if movement between modules occurs in an integral multiple of a common block of time. The number of different modules, some of which may contain identical chemical compositions, may be at least any integer from four to ten.

In accordance with the invention, variations on the above embodiments are envisioned. Various configurations of the tissue processing system are possible, and optional modules may be connected to form a portion of the system. The specific configuration chosen may be dictated by the average number of specimens that will be processed on a daily basis by the clinical laboratory, and/or the speed with which histology or pathology reports must be prepared.

The system may incorporate a conventional microwave oven, the improved microwave unit of the invention, or any combination thereof.

The system may be manually operated or automated. Manual operation is particularly suited for research and development because variations in the process or apparatus may be quickly assessed. For automated instruments, tissue specimens may be transported by armature or track conveyance and/or chemical compositions may be transferred by corrosion-resistant plumbing. Thus, tissue processing may be automated by moving tissue specimens between stationary modules in a particular sequence for set times, filling and emptying modules of different chemicals such that stationary tissue specimens are incubated in a particular sequence for set times, or any combination thereof.

The armature conveyance may, for example, grab the specimen with a pincer-like mechanism or catch the specimen with a hook-like device. The arm may be articulated to perform human-like motion; or may be mounted in a fixed coordinate rack with linear or two dimensional movement, and optionally another dimension of movement provided by varying the height of the arm over the system. The track conveyance may be made from resilient or tacky material to fix the specimen on the track by friction, or there may be a regular series of bumps or walls to trap the specimen therebetween. The track may be formed as a continuous belt or may be a series of belts that convey the tissue specimen, with the belt put into motion with a roller or sprocket mechanism. The cassette or holder may be adapted for conveyance by having a stem (with or without a knob) to be grabbed or a loop to be caught by the arm, or by fitting within a groove or indentation in the track. Similarly, the cassette or holder may be organized in a carrier or basket for processing a large number of specimens, the carrier or basket being adapted for transport by the armature or track conveyance.

Electric motors and controllers may be used to transport a tissue specimen by the operator's real-time command or selection of a stored program. A simple mechanism of controlling the time spent by the tissue specimen in each module would be to move the tissue sample or holder thereof at a constant speed and to adjust the length of the path through each module to accommodate the intended incubation time.

The piping or flexible tubing, as well as other components of the plumbing, should resist corrosion by the chemicals used in tissue processing (e.g., polyethylene, polyvinyl chloride, Teflon, stainless steel). Mechanical or electric pumps/valves and controllers may be used to move chemical compositions in any combination from storage chamber to reaction chamber, from reaction chamber to storage chamber if the composition can be reused, from reaction chamber to waste chamber if the composition is to be flushed from the system, to fill the storage chamber, and to flush the waste chamber by the operator's real-time command or selection of a stored program. Heating a combination of plumbing components may be necessary to maintain the chemical composition at reaction temperature or to ensure that the chemical composition (e.g., paraffin-containing) is kept in a transportable fluid state. In contrast, vapor seals and/or cooling may be necessary to isolate corrosive vapors from the mechanical and electrical components of the system.

Specimens may be processed continuously and/or batch-wise.

Safety considerations and precautions for an automated instrument (e.g., alarm monitor, proximity sensor) can be incorporated into the system.

Furthermore the accessories, disposable parts (e.g., cassettes, mesh bags), and reagents that have been adapted for use in the system may also be considered as a part of the system. These specially designed instruments and apparatuses have also been described in U.S. application Ser. Nos. 60/056,102 and 09/136,292.

The present invention will have many advantages over conventional methods in the areas of the practice of pathology, patient care, biomedical research, and education.

The availability of microscopic diagnosis of tissue specimens within about one to six hours after receipt will allow rapid, or even real-time, clinical interaction between surgical intervention and pathological evaluation. For example, if 65 minutes is taken to process tissue, a stat diagnosis may be given in about two hours. This may bring about significant improvements in patient care by eliminating or reducing to a minimum patient anxiety during the wait for diagnosis of disease, prognosis, and planning for treatment.

Consequently, there will be a drastic reordering of the workflow in pathology laboratories. Clinical laboratory space, pathological expertise, and clerical and technical personnel will be utilized more efficiently. Continuous workflow will improve accessibility and responsiveness of pathologists who process and evaluate specimens, reduce the number of pathologists needed to process and evaluate specimens, and may also improve medical education, particularly the accessibility and responsiveness of residency programs.

The smaller volume of reagents will also result in cost savings. Elimination of formaldehyde and xylene, and the diminished requirement for other hazardous chemicals, will provide benefits to the environment and increased safety in the laboratory. The costs involved in handling and disposal of hazardous chemicals will be reduced.

Standardization of tissue fixation and processing procedures will ease comparison of specimens from different laboratories. Artifacts in histology due to the use of formaldehyde and/or prolonged processing will be eliminated;

thus, allowing more precise evaluation of microscopic morphology of normal and diseased tissues. Similarly, antigen retrieval and staining will be improved. For genetic analysis, formaldehyde-induced DNA mutations will be eliminated and extraction of nucleic acid from archival material may be enhanced. The feasibility of RNA studies from stored, fixed paraffin-embedded tissue opens unlimited avenues for diagnostic and research applications.

All books, articles, applications, and patents cited in this specification are incorporated herein by reference in their entirety.

The following examples are meant to be illustrative of the present invention, but the practice of the invention is not limited or restricted in any way by them. N.B. Energy Beam Sciences' tissue microwave processors are examples of conventional microwave ovens that are available for commercial use.

EXAMPLES

Example 1

Thick tissues were sliced to a maximum of 2 mm, preferably 1.5 mm or less. Two mm thick or thinner slices, or small biopsies of fresh or previously fixed tissue were held in tissue cassettes and placed in a non-aqueous first solution of:

40% isopropyl alcohol,
40% acetone,
20% polyethylene glycol (average molecular weight 300), and
1% dimethyl sulfoxide (DMSO) (i.e., 10 ml per liter of the above mixture).

Tissues specimens were incubated for 15 minutes at a glycerin bath temperature between 45° C. and 50° C. The 400 ml solution for fixation was placed in a 500 ml beaker in a water bath shaker (linear displacement of 5 cm/sec). Additional agitation of the fixation solution was provided by bubbling with an air pump.

Fixation, dehydration, fat removal, clearing, and impregnation are accomplished by sequential exposure of the tissue specimen to three different solutions (i.e., the second, third, and fourth solutions described below), one in each of three microwave ovens from Energy Beam Sciences. A one liter solution of 70% isopropyl alcohol and 30% polyethylene glycol (average molecular weight 300) is placed in the first oven (model H2800) in a 1500 ml beaker, the solution in the second oven (model H2800) consists of one liter of 70% isopropyl alcohol and 30% xylene in a 1500 ml beaker, and the third oven (model H2500) contains a solution of 1000 ml of xylene and 300 gm of paraffin in a 1500 ml beaker. Ten ml of DMSO per liter are added to these three solutions. Heating at 60° C. by microwave radiation is effected for 15 minutes in the first oven, and 5 minutes each in the second and third ovens (75% power setting with a cycle of 2 seconds).

To continue paraffin impregnation after completion of the microwave radiation steps, tissue sections were incubated in four 500 ml baths of molten paraffin placed within a large dessicator filled with paraffin, and resting in a glycerin bath at 75° C. Tissue sections were transferred from one paraffin bath to the next at 3 minute intervals, for a total impregnation time of 12 minutes. Each 3 minute interval was measured from the time that the pressure reading is about 640 mm of Hg. No agitation was used in this step.

Example 2

Fixation, dehydration, fat removal, and paraffin impregnation of fresh or fixed tissue sections, approximately 1 mm thick, was accomplished in 40 minutes by exposing these tissue sections to four successive steps as follows.

Step 1.

In this example, the first solution consisted of:

60% isopropyl alcohol,
10% acetone,
30% polyethylene glycol (average molecular weight 300), and
dimethyl sulfoxide (DMSO) added at an approximate concentration of 1% of the total volume. One liter of this solution suffices to fix 60 specimens of tissue held in tissue cassettes. The specimens were incubated at 55° C. in a commercial tissue microwave processor (H2500 or H2800, Energy Beam Sciences) for 5 min each in a series of three baths containing the first solution (15 min total incubation); agitation of the solution was obtained by bubbling to accelerate solution exchange.

Step 2.

The specimens were incubated in a solution of 70% isopropyl alcohol, 30% acetone, and DMSO added at an approximate concentration of 1% at 60° C. Specimens were heated in a commercial tissue microwave processor (H2800, Energy Beam Sciences) for 5 min each in two beakers containing the solution (10 min total incubation), which were agitated by bubbling.

Step 3.

Following microwave irradiation, impregnation was initiated by incubation in a wax solution of 25% mineral oil and 75% molten paraffin placed in a large dessicator resting in a 60° C. or 70° C. glycerin bath, under a vacuum of about 200 mm of Hg, for 5 min. Paraffin was degassed prior to use as described in Example 1.

Step 4.

Impregnation was completed by incubation in four baths of molten paraffin placed within a large dessicator resting in a glycerin bath at 75° C. Tissue sections were transferred from one paraffin bath to the next at 3 min intervals, for a total impregnation time of 12 min. Each 3 min interval was measured for the time that the pressure reading is about 640 mm of Hg.

In this example, 6 ml of a color indicator stock solution (10 gm methylene blue in 1000 ml of isopropyl alcohol) was added to each of the solutions of isopropyl alcohol and acetone. Tissue specimens acquire a blue tint that facilitates their handling during impregnation and handling; penetration of the tissue specimen may also be monitored by observation of an even blue color throughout the tissue specimen.

Example 3

Fixation, dehydration, fat removal, and paraffin impregnation of fresh or fixed tissue sections, up to about 1 to 2 mm thick, were accomplished in about 65 minutes as follows. Sections of 1.5 mm or less are preferred for consistency.

Step 1.

In this example, the first solution consists of:

40% isopropyl alcohol,
40% acetone,
20% polyethylene glycol (average molecular weight 300),
glacial acetic acid added at an approximate concentration of 0.5% of the total volume, and
dimethyl sulfoxide (DMSO) added at an approximate concentration of 1% of the total volume. One liter of this solution suffices to fix 60 specimens of tissue held in tissue cassettes. The specimens are incubated at 65° C. in a commercial tissue microwave processor (H2500 or H2800, Energy Beam Sciences) for 15 min in a 1500 ml beaker containing the first solution; agitation of the solution is obtained by bubbling to accelerate solution exchange.

Step 2.

The specimens are incubated in a solution of 55% isopropyl alcohol, 25% acetone, 10% polyethylene glycol (average molecular weight 300), 10% low viscosity mineral oil, glacial acetic acid added at an approximate concentration of 0.5% of the total volume, and DMSO added at an approximate concentration of 1%. Specimens are heated at 65° C. in a commercial tissue microwave processor (H2800, Energy Beam Sciences) for 15 minutes in a 1500 ml beaker containing the solution, which is agitated by bubbling.

Step 3.

The specimens are incubated in a solution of 55% isopropyl alcohol, 25% acetone, 20% low viscosity mineral oil, glacial acetic acid added at an approximate concentration of 0.5% of the total volume, and DMSO added at an approximate concentration of 1% of the total volume. Specimens are heated at 65° C. in a commercial tissue microwave processor (H2800, Energy Beam Sciences ) for 5 minutes in a 1500 ml beaker containing the solution, which is agitated by bubbling.

Step 4.

Following microwave irradiation, impregnation is initiated by incubation in two baths of a wax solution of 30% low viscosity mineral oil and 70% molten paraffin placed in a large dessicator resting in a 60° C. glycerin bath, under a vacuum of about 640 mm of Hg, for 5 minutes in each bath.

Step 5.

Impregnation is completed by incubation in four baths of molten paraffin placed within a large dessicator resting in a glycerin bath at about 75° C. to 80° C. and a reduced pressure of about 640 mm of Hg, for 5 minutes each. Tissue specimens were transferred from one paraffin bath to the next at 5 minute intervals, for a total impregnation time of 20 minutes. Each 5 minute interval was measured for the time that the pressure reading is about 640 mm of Hg.

Example 4

Figure 12:
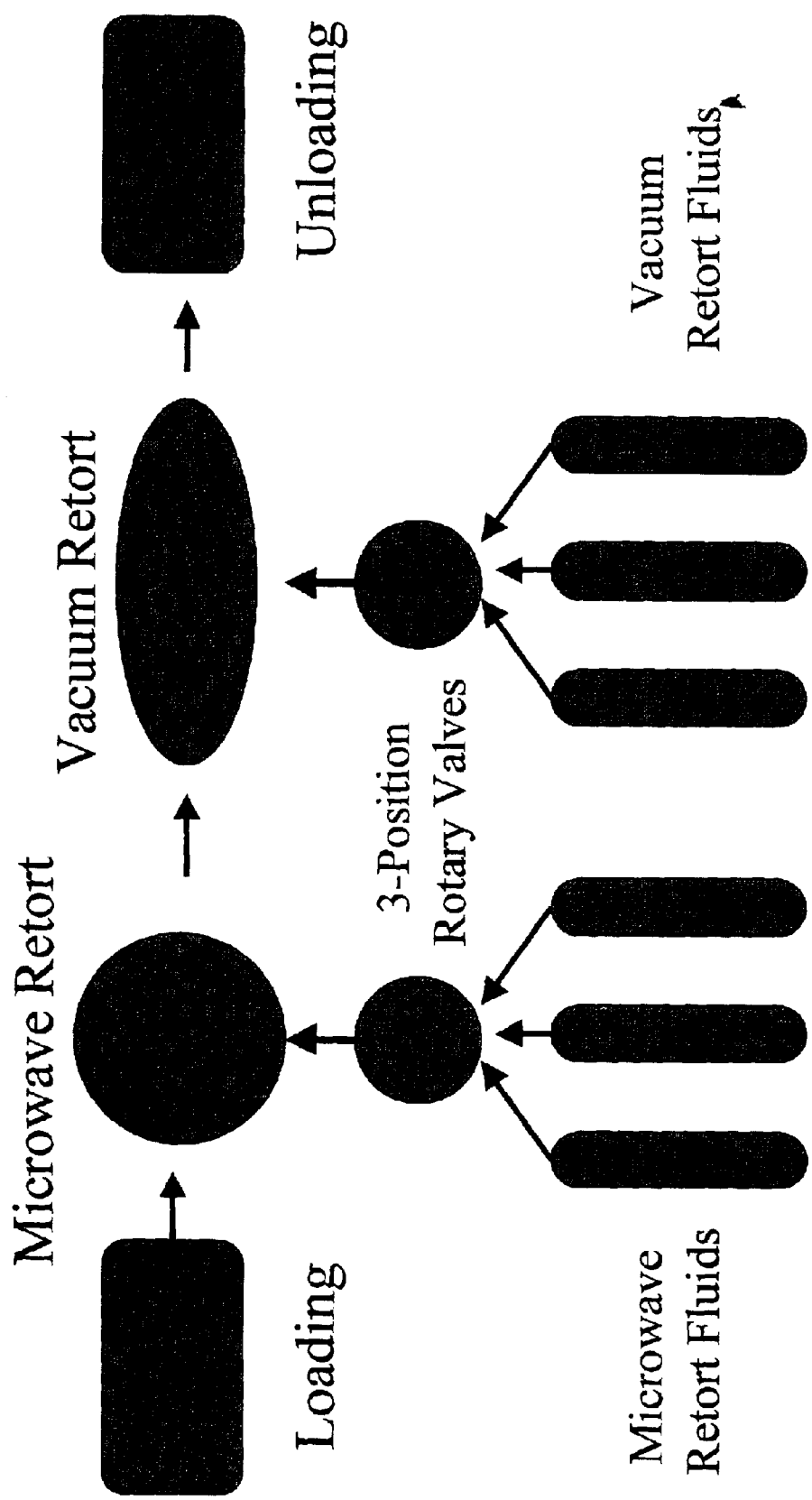
FIG. 12 is a schematic illustration of an alternative tissue processing system of the invention.

Tissue processing may be performed in the following manner using the system illustrated in FIG. 12. Fluid levels in the reservoirs are checked, retorts are cleaned, and plumbing is flushed prior to operation. Vacuum is drawn and air pressure is raised to transfer solutions and, if needed, provide agitation of solutions within the retort by P/V cycling. Only impregnation in the vacuum retort requires a reduction in the pressure because tissue processing in the microwave retort (e.g., hardening and initial impregnation) is done at atmospheric pressure. Solutions and retorts are warmed to appropriate operating temperatures.

Figure 13:
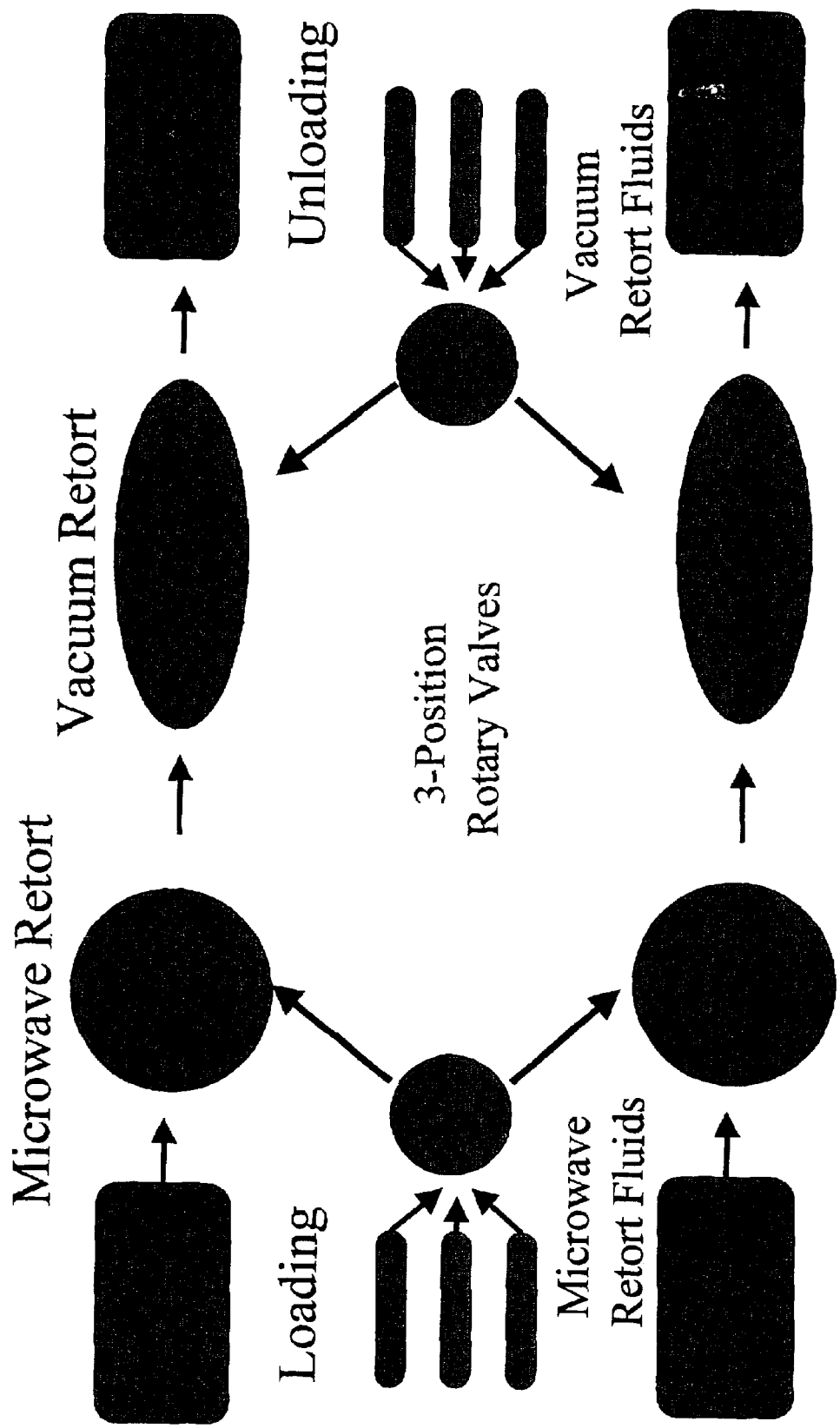
FIG. 13 is a schematic illustration of an alternative tissue processing system of the invention (i.e., two series of modules arranged for parallel processing).

A basket containing samples in cassettes is loaded. If the system illustrated in FIG. 13 is being used, then tissue processing can be performed in parallel because each series of retorts can be accessed independently. An arm or track moves the loaded basket from the loading station to the microwave retort, and then to the vacuum retort. Retorts may resemble the reaction chamber shown in FIGS. 8 and 11 for hardening and impregnation, respectively: no beaker insert is used and the lid is attached to the rest of the reaction chamber by a hinge. The lid can be moved aside (e.g., by grabbing a handle on the top of the lid) to open the reaction chamber. This allows access to the interior without having to rest the lid at a holding station. Finally, when tissue impregnation is completed, the loaded basket is moved from the vacuum retort to an unloading station containing molten paraffin. The time required to transfer the basket between stations is less than about 10 seconds. The tissue cassettes can then be unloaded from the basket.

The reaction chamber containing an impregnation agent (e.g., mineral oil, wax) may be heated using a common heating source. Alternatively, a heater maintains the temperature of water circulating in tubing in contact with the impregnation agent to keep it in a molten state. The hot water can be circulated to each station for which it is needed; each reaction chamber can be attached to a supply and return manifold. For example, a coil of tubing can be located inside the reaction chamber; this heating coil would then transfer heat to the contents. Preferably the heating coil is eliminated by wrapping the outside wall of the reaction chamber with electrical wire that conducts heat through the walls into the contents of the reaction chamber.

The process described in Example 3 may be used in this system. Each different solution is stored in one of three reservoirs and can be transferred to or from the retort. For example, a three-position rotary valve can select the appropriate reservoir for that step and pumping at nominal pressures of 250 mm Hg can transfer solution into the retort while 0.35 Kg/cm$^2$ can transfer solution out of the retort; agitation can be performed by P/V cycles of nominal pressure 0.35 Kg/cm$^2$ and 500 mm Hg vacuum. The connections (e.g., flexible tubing) between reservoirs and retorts, and the port where the connection joins each reservoir or retort, are not shown. Other conditions (e.g., times or temperatures for each step) are as described in Example 3.

Example 5

Detection of Antigen in Tissue Sections

Paraffin sections are cut on a microtome to a thickness of 3 microns, placed in a water bath, and floated onto a glass slide. Paraffin was melted by placing slides in either a 58° C. oven for 30 minutes, or preferably in a 37° C. oven for approximately 18 hours or overnight, and then dewaxed in a xylene bath for 10 minutes. Slides were rehydrated in decreasing ethanol solutions for 1 min each (two baths of absolute, two baths of 95%, and one bath of 90%) and rinsed by submerging in tap water for 2 minutes.

Endogenous peroxidase was blocked with a solution of 6% hydrogen peroxide ($H_2O_2$) and methanol, or 35 ml of 6% $H_2O_2$ with 140 ml of methanol, incubated for 15 minutes. Slides were rinsed by submerging in tap water for 2 minutes and PBS for 2 minutes, then dried.

Slides were transferred to a humidity chamber and normal horse serum (NHS) was added to block for 10 minutes. Excess normal horse serum was decanted from slides, and specific primary antibody was incubated for 30 minutes on the tissue section in a humidity chamber at room temperature. Slides were flushed with PBS with back and forth motion using a squeeze bottle, submerged in a PBS bath for 2 minutes, and excess PBS was dried off each slide. Linking solution (also known as secondary antibody or biotinylated anti-rabbit or anti-mouse) was added to each tissue section and incubated for 25 minutes in a humidity chamber at room temperature. Such rabbit, rat, and mouse secondary antibodies (e.g., anti-IgM, anti-IgG) were obtained from Dako (Carpinteria, Calif.) and used at a dilution of about 1:600. Slides were flushed with PBS using a squeeze bottle, submerged in a PBS bath for 2 minutes, and excess PBS was dried off each slide.

Signal was developed according to the manufacturer's instructions (Vector Laboratories). Avidin-biotin complex (ABC) solution was added to the tissue section and incubated for 25 minutes in humidity chamber. Slides were flushed with PBS in a squeeze bottle and submerged in a rack in a PBS bath for 2 minutes. The rack was submerged in a bath of diaminobenzidine (DAB) chromogen for 6 minutes, then submerged under running water to wash gently for 4 minutes. Tissue sections were counterstained with hematoxylin (staining time will depend on the age of the hematoxylin) from about 15 seconds to 90 seconds at room temperature. Slides were washed under running water for 3 minutes to remove excess counterstain, dehydrated in alcohol baths (about 10 seconds in each) from 85% to 100%, cleaned in xylene, and coverslipped.

Better antigen reactivity has been shown for progesterone receptor, factor VIII-related antigen, CD-31, CD-68, cytokeratin-7, chromogranin, and smooth muscle antigen, probably because of better preservation of antigen (e.g., greater signal-to-noise ratio).

TABLE 1

| Reagents | Catalog # | Source |
| --- | --- | --- |
| Microscope slides - snow coat X-TRA | 00206 | Surgipath |
| Elite ABC Kit (standard) | PK-6100 | Vector Labs. |
| Biotinylated anti-mouse IgG (H&L) | BA-2000 | Vector Labs. |
| Biotinylated anti-mouse IgM (H&L) | BA-2020 | Vector Labs. |
| Biotinylated anti-mouse/anti-rabbit IgG (H&L) | BA-6000 | Vector Labs. |
| Normal horse serum (NHS) | S-2000 | Vector Labs. |
| Diaminobenzidine tetrahydrochloride | K3466 | DAKO Corp. |
| Potassium phosphate (monobasic) | 7100-500 NY | Baxter Scientific |
| Sodium phosphate (dibasic) | 7917-2.5 NY | Baxter Scientific |
| Sodium chloride (AR Crystals) | 7581-2.5 NY | Baxter Scientific |
| 30% Hydrogen peroxide | 5240-500 NY | Baxter Scientific |
| Xylene | 8644-20 NY | Baxter Scientific |
| Harris hematoxylin | S-7735-3 | Baxter Scientific |
| Methyl alcohol | 3016-20 NY | Baxter Scientific |
| 95% Alcohol | | Florida Distillers |
| Absolute Ethyl Alcohol | | Florida Distillers |

TABLE 2

Antibodies, Dilutions and Incubation Times

| Rabbit (R) | Microwave (M) | 30' Incubation |
| --- | --- | --- |
| Mouse (MIgG) | Trypsin (T) | 45' Incubation |
| Mouse (MIgM) | Protease (P) | 90' Incubation |
| Goat (G) | Fast Green (FG) | |

TABLE 3

Antibodies, Dilutions and Incubation Times

| Abbrev. | Antibody | Special Procedure | Incub. Time | Linking Sol. |
| --- | --- | --- | --- | --- |
| (ACTH) | Adrenocorticotropin Hormone | 1:2000 | 30' | R |
| (AACT) | Alpha-1 Antichymotrypsin | 1:50000 | 30' | R |
| (AAT) | Alpha-1 Antitrypsin | 1:2000 | 30' | R |
| (ADENO) | Adenoviurs | 1:1000 | 30' | MIgG |
| (AFP) | Alpha Fetoprotein | 1:2500 | 30' | R |
| (AEI/3) | Cytokeratin | 1:200(M) | 45' | MIgG |
| (ALA) | Alpha Lactalbumin | 1:600 | 30' | R |
| (ACTIN) | Actin Muscle | 1:200 | 30' | MIgG |
| (APP-A4) | Anti-Alzheimer Precursor Protein A4 | 1:500(M) | 45' | MIgG |
| (ASPE) | Aspergillus | 1:500 | 30' | R |
| (AR) | Androgen Receptor | 1:20(M) (FG) | 45' | MIgG |
| (BCA) | B-Cell | 1:200 | 30' | MIgG |
| (bcl-2) | Anti-Human Oncoprotein | 1:100(M) | 45' | MIgG |
| (BerEp4) | Human Epithelial Antigen | 1:25 | 30' | MIgG |
| (B72.3) | TAG72 Tumor-Associated Glycoprotein 72 | 1:100 | 30' | MIgG |
| (BLA36) | B Lymphocyte Antigen | 1:100 | 30' | MIgG |
| (CMV) | Cytomegalovirus | 1:50(P) | 30' | MIgG |

TABLE 3-continued

Antibodies, Dilutions and Incubation Times

| Abbrev. | Antibody | Special Procedure | Incub. Time | Linking Sol. |
| --- | --- | --- | --- | --- |
| (CHRG) | Chromogranin | 1:50 | 30' | MIgG |
| (CALC) | Calcitonin | 1:2000 | 30' | R |
| (CEA) | Carcinoembryonic Antigen | 1:6000 | 30' | R |
| (CERb'B2) | c-erbB-2 Oncogene Mab1 | 1:1500 | 90' | R |
| (CATH) | Cathepsin D | 1:2000(M) | 45' | R |
| (CAM 5.2) | Cytokeratin | 1:500(M) | 45' | R |
| (CK 7) | Cytokeratin | 1:200(M) | 45' | MIgG |
| (CK 20) | Cytokeratin | 1:25(M) | 45' | MIgG |
| (COLL IV) | Collagen IV | 1:25(P) | 30' | MIgG |
| (CA 125) | Anti-Human CA 125 (MII) | 1:20(M) | 45' | MIgG |
| (CD 30) | Anti-Human Ki-1 Antigen (BER-H2) | 1:200(M) | 45' | MIgG |
| (ER) | Estrogen Receptor | 1:50(M) (FG) | 45' | MIgM |
| (FVIII) | Von Willebrand Factor | 1:50(P) | 30' | MIgM |
| (FSH) | Follicle Stimulating Hormone | 1:3000 | 30' | R |
| (5 HT) | Serotonin | 1:50 | 30' | MIgM |
| (FXIII) | Anti-coagulation Factor | 1:1200 | 30' | R |
| (GAST) | Gastrin | 1:2000 | 30' | MIgM |
| (GFAP) | Glial Fibrillary Acidic Protein | 1:1500 | 30' | R |
| (GLUC) | Glucagon | 1:10000 | 30' | R |
| (GH) | Growth Hormone | 1:5000 | 30' | R |
| (GCDFP) | Gross Cystic Disease Fluid Protein | 1:250 | 30' | MIgM |
| (GRP) | Gastrin-Releasing Peptide | 1:1000 | 30' | R |
| (HMWK) | High Molecular Weight Keratin (34βE12) | 1:10 | 45' | MIgM |
| (Hbcore) | Hepatitis B Core Antigen | 1:5000 | 30' | R |
| (HBsAg) | Hepatitis B Surface Antigen | 1:100 | 30' | MIgM |
| (HSV I) | Herpes Simplex Type I | 1:10 | 30' | R |
| (HSV II) | Herpes Simplex Type II | 1:10 | 30' | R |
| (HCG) | Human Chorionic Gonadotropin | 1:50000 | 30' | R |
| (HPL) | Human Placental Lactogen | 1:100000 | 30' | R |
| (HIST) | Histoplasma | 1:1000 | 30' | R |
| (H.Pyl) | Heliobacter pylori | 1:500(M) | 45' | R |
| (β-HCG) | β-Human Chorionic Gonadotropin | 1:10000 | 30' | R |
| (IgA) | Alpha Heavy Chain | 1:400 | 30' | R |
| (IgG) | Gamma Heavy Chain | 1:1000 | 30' | R |
| (IgAs) | Secretory Piece of IgA | 1:200 | 30' | R |
| (IgM) | Mu Heavy Chain IgM | 1:1000 | 30' | R |
| (INS) | Insulin | 1:100 | 30' | R |
| (Ki-67) | Nuclear Antigen MIB-1 | 1:50(M) (FG) | 45' | MIgG |
| (K) | Kappa Light Chain | 1:200(M) | 45' | MIgG |
| (KERATIN) | AEI/3 CAM | 1:50/1:500 (M) | 45' | MIgG |
| (LCA) | Leucocyte Common Antigen | 1:50 | 30' | MIgG |
| (Leu M1) | Leu M1 Antigen | 1:200(M) | 45' | MIgM |
| (Leu 7) | Leu 7 Antigen | 1:50(M) | 45' | MIgM |
| (Lectin) | Lectin | 1:4000 | USE INSTEAD OF NHS | |
| (Anti-Lectin) | Anti-Lectin Antigen | 1:10000 | 30' | G |
| (LEA 135) | Anti-Human Luminal Epithehal Antigen | 1:50 | 30' | MIgG |
| (LH) | Luteinizing Hormone | 1:3000 | 30' | R |
| (L) | Lambda Light Chain | 1:6000(M) | 45' | MIgG |
| (LMK-8) | Low Molecular Weight Keratin | 1:25(M) | 45' | MIgG |
| (LIP-AS 105) | Lipase | 1:400 | 30' | MIgG |
| (MCA) | Myeloid Histiocyte Antigen (MAC 387) | 1:400(M) | 45' | MIgG |
| (MUR) | Muramidase | 1:2000 | 30' | R |
| (MYOGL) | Myoglobin | 1:5000 | 30' | R |
| (MAPH) | Macrophage | 1:50 | 30' | MIgG |
| (MTLT) | Metallothinein | 1:50 | 30' | MIgG |
| (MEL) | Melanoma HMB 45 | 1:50 | 30' | MIgG |
| (MAK 6) | Anti-Cytokeratin | 1:50(T) | 90' | MIgG |
| (MBP) | Myelin | 1:500 | 30' | R |

TABLE 3-continued

Antibodies, Dilutions and Incubation Times

| Abbrev. | Antibody | Special Procedure | Incub. Time | Linking Sol. |
|---|---|---|---|---|
| (MESO) | Mesothelial Antigen | 1:500 | 30' | MIgM |
| (MAST-C) | Mast Cell | 1:2000(T) | 30' | MIgG |
| (MPO) | Myeloperoxidase | 1:5000 | 30' | R |
| (MGN) | Myogenin | 1:15 | 45' | MIgG |
| (NB) | Neuroblastoma | 1:200 | 90' | MIgG |
| (N-FIL) | N-Filament (2F11) | 1:250 | 30' | MIgG |
| (NSE) | Neuron Specific Enolase | 1:4000(M) | 45' | MIgG |
| (PAMYL) | Pancreatic Amylase | 1:20 | 30' | MIgG |
| (PCP) | Pneumocystis carinii | 1:25 | 30' | MIgM |
| (PLAP) | Placental Alkaline Phosphatase | 1:800 | 30' | R |
| (PPP) | Pancreatic Polypeptide | 1:3000 | 30' | R |
| (PTH) | Parathyroid Hormone | 1:250(M) | 45' | (RAT) |
| (PROL) | Prolactin | 1:500 | 30' | R |
| (PAPH) | Prostatic Acid Phosphatase | 1:4000 | 30' | R |
| (PML) (SV40) | Progressive Multifocal Leucoencephalopathy | 1:10000 | 30' | R |
| (PR) | Progesterone Receptor | 1:100(M) | 45' | R |
| (PR 1A6) | Progesterone Receptor | 1:50(M) | 45' | MIgG |
| (PSA) | Prostate Specific Antigen | 1:750 | 30' | R |
| (PCNA) | Proliferating Cell Nuclear | 1:100(M) (FG) | 45' | MIgG |
| (PS2) | PS2 Protein | 1:1000 | 45' | R |
| (P53) | p53 Antigen | 1:50(M) (FG) | 45' | MLgG |
| (S100 A) | S100 A Protein | 1:3000 | 30' | R |
| (S100) | S100 Protein | 1:2000 | 30' | R |
| (SOMAT) | Somatostatin | 1:3000 | 30' | R |
| (SYNAP) | Synaptophysin | 1:800(M) | 45' | R |
| (SMA) | Smooth Muscle Actin | 1:100 | 30' | MIgG |
| (∝SR-1) | Sarcomeric Actin | 1:100 | 30' | MIgG |
| (TESTOS) | Testosterone | 1:250 | 30' | R |
| (TGB) | Thyroglobulin | 1:20000 | 30' | R |
| (TP-103) | Treponema | 1:50(T) | 30' | MIgG |
| (TM) | Thrombomodulin | 1:50 | 30' | MIgG |
| (TSH) | Thyroid Stimulating Hormone | 1:2000 | 30' | R |
| (TCA) | T-Cell Antigen | 1:800(M) | 45' | MIgG |
| (TOXO) | Toxoplasma | 1:1000 | 30' | R |
| (UBT) | Ubiquitin | 1:250 | 30' | R |
| (VIP) | Vasoactive intestinal peptide | 1:1500 | 30' | R |
| (VIM) | Vimentin | 1:800(M) | 45' | MIgG |
| (VZV) | Variecella-Zoster Virus | 1:100 | 30' | MIgG |
| (WSKER) | Wide Spectrum Keratin | 1:500 | 30' | R |

Example 6

DNA Extraction from Processed Tissue Sections

Two six micron tissue sections were placed in a 1.5 ml microfuge tube, 800 µl xylene was added and mixed by vortexing, 400 µl absolute ethanol was added and mixed by vortexing, the tube was centrifuged for 5 minutes in a high speed microfuge, and the supernatant was decanted. To the pellet, 800 µl absolute ethanol was added and mixed by vortexing.

The supernatant was decanted after centrifugation as above, and 100 µl of a detergent/proteinase K solution (1% NP40 or Triton X-100, 2.4 µl of 2.5 mg/ml proteinase K) was added to the pellet and incubated at 55° C. for one hour. Proteinase K was inactivated by incubation at 95° C. for 10 minutes. Save the supernatant containing DNA after centrifugation in the microfuge for 5 minutes. This material is ready for PCR. It should be precipitated and/or extracted further if Southern blotting is planned. More sections would be required to obtain enough DNA for restriction analysis.

Example 7

RNA Extraction from Processed Tissue Sections

Ten sections (7 µm each) of a paraffin block were cut using disposable blades. The blocks were prepared according to the present invention and by the conventional procedure. They were placed in 50 ml Falcon tubes, deparaffinized with 20 ml of xylene, and the remaining tissue was then washed twice with absolute alcohol for 30 minutes. The tissue was suspended at 0.5 gm/ml in a solution containing 4M guanidinium thiocyanate, 25 mM Na citrate pH 7.0, 0.5% N-laurylsarcosine, and 0.1 M of 2-mercaptoethanol. The solution was mixed by vortexing and DNA was sheared by passage through an 18 to 22 gauge syringe needle.

The RNA-containing solution was carefully layered on 2.8 ml of 5.7 M CsCl in several 5 ml centrifuge tubes (Sorvall), and RNA was sedimented by centrifugation in an SW55Ti rotor at 35,000 rpm and 18° C. for 14 hours in a Beckman L8-53 ultracentrifuge. The top fraction was carefully removed to leave an RNA pellet at the bottom of the tube. The pellet was resuspended with ribonuclease-free water, and the Eppendorf tube was spun at 14,000 rpm for 10 minutes. The supernatant containing RNA was saved and the ultraviolet (UV) absorbance was measured: an extinction coefficient of 1 $OD_{280}$/cm is estimated to be the equivalent of about 40 µg/ml RNA and the $OD_{260}/OD_{280}$ ratio should be between about 1.8 and about 2.0. A total of 45 µg RNA was extracted from tissue specimens prepared according to the present invention whereas no RNA was detectable from tissue specimens processed conventionally.

While the invention has been described in connection with what is presently considered to be practical and preferred embodiments, it is understood that the present invention is not to be limited to the disclosed embodiments but, on the contrary, is intended to cover various modifications and equivalent arrangements included within the spirit and scope of the appended claims. Thus, it is to be understood that variations in the described invention will be obvious to those skilled in the art without departing from the novel aspects of the present invention and such variations are intended to come within the scope of the claims below.

Furthermore, it should be understood that an element contained in this specification should not be construed as a limitation of the claimed invention unless explicitly recited in the claims. Thus, the claims are the basis for determining the scope of legal protection granted instead of using the specification to import a limitation which is not explicitly recited in the claims.

We claim:

1. A microwave unit for processing a tissue specimen of less than about three millimeters for histology comprising:
   (a) a source which generates microwave radiation as a form of energy,
   (b) a waveguide which transmits the microwave radiation, and
   (c) a first reaction chamber which receives the microwave radiation, wherein at least a first chemical composition and the tissue specimen in contact therewith are surrounded within walls of the first reaction chamber;
   wherein the microwave radiation is transmitted from the source to the first reaction chamber by the waveguide, the first reaction chamber has an interior-geometry which provides a substantially uniform distribution of temperature therewithin due to the energy of the microwave radiation, the first chemical composition is brought from a first storage chamber to the first reaction chamber, and the tissue specimen is at least initially hardened by the first chemical composition, the microwave radiation, or both.

2. The microwave unit of claim 1 further comprising:

(d) a closure adapted to isolate the first reaction chamber, (e) thermal insulation surrounding the first reaction chamber, (f) an agitator within the first reaction chamber to promote chemical exchange between the tissue specimen and the first chemical composition, and (g) a port adapted to fill the first reaction chamber with the first chemical composition from the first storage chamber and to empty the first reaction chamber.

3. The microwave unit of claim 1 configured such that the temperature of a solution within the first reaction chamber is maintained between about 5° C. and about 70° C.

4. The microwave unit of claim 1, wherein the first chemical composition is a non-aqueous solution comprised of a fixative and a dehydrating agent.

5. The microwave unit of claim 4, wherein the non-aqueous solution is comprised of a ketone and an alcohol.

6. The microwave unit of claim 5, wherein the non-aqueous solution has a volume ratio of alcohol to ketone in a range between about 1:3 and 3:1.

7. The microwave unit of claim 4, wherein the non-aqueous solution is further comprised of polymers between about 100 and 500 average molecular weight and a surfactant.

8. The microwave unit of claim 4, wherein the tissue specimen is brought into contact with a series of at least two different chemical compositions which are non-aqueous solutions comprised of a ketone and an alcohol, wherein the volume ratio of alcohol to ketone changes between at least two non-aqueous solutions of the series.

9. The microwave unit of claim 1 configured such that the tissue specimen is substantially hardened by a plurality of different chemical compositions, the microwave radiation, or both.

10. The microwave unit of claim 1 configured such that the tissue specimen is substantially hardened in less than about 30 minutes.

11. The microwave unit of claim 1 configured such that the tissue specimen is substantially hardened in less than about two hours.

12. The microwave unit of claim 1, wherein the source is a magnetron generating microwave radiation with a frequency between 2425 and 2575 megahertz.

13. The microwave unit of claim 1, wherein the first reaction chamber comprises a whispering gallery mode which provides substantially uniform distribution of temperature in a solution within the first reaction chamber.

14. The microwave unit of claim 1 comprising a plurality of reaction chambers, each of said reaction chambers being connected by the waveguide to the source.

15. A system for processing a tissue specimen of less than about three millimeters for histology comprising a plurality of modules each comprised of a reaction chamber and a chemical composition contained therein, wherein the tissue specimen is processed by being brought into contact with each chemical composition in the reaction chamber of each module:

(a) at least one first module comprising a microwave unit of claim 1, wherein at least a second chemical composition is brought from a second storage chamber to the first reaction chamber and the tissue specimen is thereby at least initially impregnated;

(b) at least one second module comprising a second reaction chamber, wherein impregnation of the tissue specimen is substantially completed under less than atmospheric pressure within walls of the second reaction chamber; and (c) a conveyance which transfers the tissue specimen between a said first module and a said second module.

16. The tissue processor system of claim 15, wherein the conveyance comprises a track connecting the said first module and the said second module.

17. The tissue processor system of claim 15, wherein the conveyance comprises an armature connecting the said first module and the said second module.

18. The tissue processor system of claim 15 further comprised of:

(d) a closure adapted to isolate the second reaction chamber, (e) thermal insulation surrounding the second reaction chamber, (f) a heater which maintains wax in molten form in the second reaction chamber, and (g) a port adapted to fill the second reaction chamber with a molten wax solution.

19. The tissue processor system of claim 15 configured such that the temperature of a solution within the second reaction chamber is maintained between about 50° C. and about 70° C.

20. The tissue processor system of claim 15, wherein the second chemical composition is a non-aqueous solution comprised of fixative, dehydrating agent, and impregnating agent.

21. The tissue processor system of claim 15, wherein the second chemical composition is a non-aqueous solution comprised of a ketone, an alcohol, and mineral oil.

22. The tissue processor system of claim 15, wherein there are at least four different chemical compositions in separate storage chambers in fluid communication with at least said first module and at least one said second module.

23. The tissue processor system of claim 15, wherein there are at least two parallel series of modules of the (a) and (b) types, and transfer of tissue specimens within a series of modules is independently controlled.

24. The tissue processor system of claim 15 configured such that a tissue specimen is substantially impregnated by wax in less than about 25 minutes.

25. The tissue processor system of claim 15 configured such that a tissue specimen is substantially impregnated by wax in less than about two hours.

26. A microwave unit for tissue processing comprising:

(a) a source generating microwave radiation, (b) a reaction chamber comprising an interior geometry to provide a substantially uniform distribution of microwave radiation transmitted therein, (c) a waveguide transmitting the microwave radiation from the source to the reaction chamber, (d) a first storage chamber in fluid communication with the reaction chamber, wherein a first non-aqueous solution comprising an admixture of at least fixative and dehydrating agent is transferred between the first storage chamber and the reaction chamber, and (e) a second storage chamber in fluid communication with the reaction chamber, wherein a second non-aqueous solution comprising an admixture of at least fixative and dehydrating agent is transferred between the second storage chamber and the reaction chamber, and (f) a third storage chamber in fluid communication with the reaction chamber, wherein a third non-aqueous solution comprising an admixture of at least fixative, dehydrating agent, and impregnating agent is transferred between the third storage chamber and the reaction chamber;

wherein tissue hardening is at least initiated in the reaction chamber by contact with the first non-aqueous solution, the microwave radiation, or both; the volume ratio between dehydrating agent and fixative increases from the first non-aqueous solution to the second non-aqueous solution; tissue impregnation is at least initiated in the reaction chamber by contact with the third non-aqueous solution; and the reaction chamber further comprises an agitator and a heater which increase rates for tissue hardening and tissue impregnation.

27. The microwave unit of claim 26 further comprising a multi-position rotary valve and a pump which controls fluid transfer between the storage chambers and the reaction chamber by pressure/vacuum cycles.

28. The microwave unit of claim 26 configured such that pressure within the reaction chamber is maintained above about 500 millimeters of Hg.

29. A microwave unit for processing a tissue specimen for histology comprising:
   (a) a source which generates microwave radiation as a form of energy,
   (b) a waveguide which transmits the microwave radiation, and
   (c) a first reaction chamber which receives the microwave radiation, wherein the tissue specimen is at least initially hardened therewithin;

wherein the microwave radiation is transmitted from the source to the first reaction chamber by the waveguide, and the first reaction chamber comprises a whispering gallery mode which provides substantially uniform distribution of temperature in a solution within the first reaction chamber due to the energy of the microwave radiation.

30. A system for processing a tissue specimen for histology comprising a plurality of modules each comprised of a reaction chamber and a chemical composition contained therein, wherein the tissue specimen is processed by being brought into contact with each chemical composition in the reaction chamber of each module:
   (a) at least one first module comprising a microwave unit of claim 29, wherein the tissue specimen is further at least initially impregnated within the first reaction chamber;
   (b) at least one second module comprising a second reaction chamber, wherein impregnation of the tissue specimen is substantially completed under less than atmospheric pressure within the second reaction chamber; and
   (c) a conveyance which transfers the tissue specimen between a said first module and a said second module.

31. A microwave unit for tissue processing comprising:
   (a) a source generating microwave radiation,
   (b) a reaction chamber comprising a whispering gallery mode which provides substantially uniform distribution of microwave radiation transmitted therein,
   (c) a waveguide transmitting the microwave radiation from the source to the reaction chamber,
   (d) a first storage chamber in fluid communication with the reaction chamber, wherein a first non-aqueous solution comprising an admixture of at least fixative and dehydrating agent is transferred between the first storage chamber and the reaction chamber, and
   (e) a second storage chamber in fluid communication with the reaction chamber, wherein a second non-aqueous solution comprising an admixture of at least fixative and dehydrating agent is transferred between the second storage chamber and the reaction chamber, and
   (f) a third storage chamber in fluid communication with the reaction chamber, wherein a third non-aqueous solution comprising an admixture of at least fixative, dehydrating agent, and impregnating agent is transferred between the third storage chamber and the reaction chamber;

wherein tissue hardening is at least initiated in the reaction chamber by contact with the first non-aqueous solution, the microwave radiation, or both; the volume ratio between dehydrating agent and fixative increases from the first non-aqueous solution to the second non-aqueous solution; tissue impregnation is at least initiated in the reaction chamber by contact with the third non-aqueous solution; and the reaction chamber further comprises an agitator and a heater which increase rates for tissue hardening and tissue impregnation.

32. The microwave unit of claim 1, wherein tissue specimen is about 1 mm to about 3 mm thick.

33. The tissue processor system of claim 15, wherein tissue specimen is about 1 mm to about 3 mm thick.

* * * * *